United States Patent [19]

Inokuchi et al.

[11] Patent Number: 5,763,438
[45] Date of Patent: Jun. 9, 1998

[54] 2-ACYLAMINOPROPANOL COMPOUND AND MEDICAL COMPOSITION

[75] Inventors: Jinichi Inokuchi; Masayuki Jinbo; Takayuki Nagai; Haruki Yamada, all of Tokyo, Japan

[73] Assignee: Seikagaku Corporation, Japan

[21] Appl. No.: 750,699

[22] PCT Filed: Jun. 7, 1995

[86] PCT No.: PCT/JP95/01143

§ 371 Date: Dec. 9, 1996

§ 102(e) Date: Dec. 9, 1996

[87] PCT Pub. No.: WO95/34530

PCT Pub. Date: Dec. 21, 1995

[30] Foreign Application Priority Data

Jun. 10, 1994 [JP] Japan ............................. 6-128734

[51] Int. Cl.$^6$ ............... A61K 31/16; A61K 31/535; C07D 295/14; C07C 233/35
[52] U.S. Cl. ............... 514/237.8; 514/625; 544/58.1; 544/168; 544/400; 546/221; 546/233; 546/234; 548/550
[58] Field of Search ............... 544/168; 554/55; 514/237.8

[56] References Cited

U.S. PATENT DOCUMENTS 5,041,441 8/1991 Radin et al. .
5,302,609 4/1994 Shayman et al. .

FOREIGN PATENT DOCUMENTS 3255073 11/1991 Japan .
6503092 12/1993 Japan .
5508851 4/1994 Japan .

OTHER PUBLICATIONS

J. Lipid Res.,vol. 28, pp. 565–571 (1987).
J. Biochem, vol. 110, pp. 96–102 (1991).
J. Cell. Physiol.,vol. 141, pp. 573–583 (1989).
J. Biochem., vol.111, pp. 191–196 (1992).
Anal. Biochem., vol. 204, pp.265–272 (1992).
J. Biochem. vol. 117, pp. 766–773 (1995).
J. Lipid Res. vol.32, pp.713–722 (1991).
Biochemical & Biophysical Research Comm., 222, pp.494–498 (1996).
J. Neurochem. vol. 67, No. 5, pp.1821–1830 (1996).
TIGG, vol. 3, No. 11, pp. 200–213 (May 1991).
Tetrahedron, vol. 48, No. 28, pp.5855–5860 (1992).
Journal of Lipid Research, vol.35, pp.1232–1240 (1994).

*Primary Examiner*—Robert W. Ramsuer
*Attorney, Agent, or Firm*—Bierman, Muserlian and Lucas

[57] ABSTRACT

This invention relates to a 2-acylaminopropanol compound represented by the formula (I):

$$R^1-CH-CH-CH_2-R^2 \quad (I)$$
$$\phantom{R^1-CH-}| \phantom{CH-}|$$
$$\phantom{R^1-CH-}OH \phantom{CH}NHCOCH(CH_2)_nCH_3$$
$$\phantom{R^1-CH-CH-CH_2-}|$$
$$\phantom{R^1-CH-CH-CH_2-}R^{11}$$

(wherein $R^1$ represents a phenyl group which may be substituted by 1 to 3 same or different substituents selected from alkyl, alkoxy, hydroxyl, hydroxyalkyl and nitro, $R^2$ represents the following formula (II), (III), (IV), (V) or (VI), (II) $-N(R^3)(R^4)$ (III) $-N$ with ring $(CH_2)_m$ and $R^5$ (IV) $-N$ with ring $(CH_2)_p$ and X (V) $-N^+$ pyridinium with $R^6$ (VI) $-NH-R^7-N(R^8)(R^9)$ (wherein $R^3$, $R^4$, $R^5$, $R^6$, $R^7$, $R^8$, $R^9$, m and p are those defined in the specification) $R^{11}$ represents a hydrogen atom or a hydroxyl group, and n represents an integer of 3 to 15) or a pharmaceutically acceptable salt thereof.

27 Claims, 6 Drawing Sheets

2-ACYLAMINOPROPANOL COMPOUND AND MEDICAL COMPOSITION

TECHNICAL FIELD

This invention relates to a 2-acylaminopropanol compound which is a ceramide analogue, and a medical composition which contains the same as an active ingredient and exhibits effects as an antiviral agent or an agent for treating neuronal diseases.

BACKGROUND ART

It has been known that glycosphingolipids (hereinafter referred to as GSL) in which various sugars such as glucose, galactose, sialic acid, etc. are bound to a ceramide molecule exist as a constitutional component of cell surface membranes of mammal cells and they are closely related to a cellular function such as development, growth, differentiation, neoplastic transformation, immunoreaction, etc. through a receptor function of a physiologically active substance, an intercellular mutual recognition and interaction, etc.

Also, it has been known that in many infections by virus and bacteria, GSL is concerned in binding with them as a receptor of host cells, and particularly glucosylceramide described below binds to virus such as adenovirus, herpes virus, influenza virus, mumps virus, Sendai virus, rabies virus, rotavirus, Reovirus and HTLV virus (K-A Karlson, Trends in Pharmacol. Sci., vol. 12, pp. 265–272 (1991)). Further, there has been suggested possibility that galactosylceramide functions as a receptor of host cells with regard to human immunodeficiency virus (HIV) (Science, vol. 253, pp. 320–323 (1991)).

GSL is a complex glycolipid consisting of a ceramide long-chain aliphatic acid wherein ($C_{13}H_{27}$—CH=CH—CH(OH)—CH(NHCOR)—$CH_2OH$) links to an amino group of a sphingosine base via acid amide bonding and a hydrophilic sugar chain portion. Nearly 300 kinds of molecular species of GSL which are different in a sugar chain structure binding to a ceramide have been found and can be roughly classified into 6 basic sugar chain series (gala series, globo series, isoglobo series, lacto series, neolacto series and ganglio series). Among the above series, 5 series of GSL except for gala series are biosynthesized from glucosylceramide enzymatically produced by using ceramide and uridine diphosphate-glucose as a starting substance and further adding various sugars thereto.

Therefore, antagonistic inhibition of binding of a receptor of GSL such as glucosylceramide and/or galactosylceramide, etc. on the surface of a host cell membrane and virus leads to development of an antiviral agent showing a wide spectrum having an effect on viral infectious diseases.

The present inventors have previously found and reported that a 2-acylaminopropanol compound having a morpholino group, such as 1-phenyl-2-decanoylamino-3-morpholino-1-propanol (hereinafter referred to as PDMP), etc. has an antiviral activity (Seikagaku vol. 65(8), p. 695 (1993)).

On the other hand, gangliosides are GSL containing sialic acid, and it is said that it has an activity to recoveries from injury of peripheral nerves and a disorder of central nervous system, i.e., acceleration of regeneration of neurons and a process of neurotransmission. Heretofore, effectiveness of exogenous gangliosides to various neuronal disease models has been investigated.

The present inventors have synthesized novel compounds into which other nitrogen-containing substituent is introduced in place of the above morpholino group and examined an antiviral activity thereof to find that they have a further strong antiviral activity as compared with the above PDMP, etc.

An object of the present invention is to provide a new type of an antiviral agent using such a novel 2-acylaminopropanol compound.

Another object of the present invention is to provide an agent for treating various diseases caused by disorders of central nervous system or peripheral nervous system, using a novel 2-acylaminopropanol compound which accelerates biosynthesis of endogenous GSL, particularly gangliosides in neurons.

DISCLOSURE OF THE INVENTION

The present inventors have studied variously in order to develop an antiviral agent based on a new mechanism and consequently found that a specific 2-acylaminopropanol compound which is a ceramide analogue exhibits an antiviral activity, to accomplish the present invention.

Also, the present inventors have studied variously in order to develop an agent for treating neuronal diseases based on a new mechanism and consequently found that specific 2-acylaminopropanol compounds accelerate biosynthesis of GSL and significantly accelerate neurite extension and synapse formation, to accomplish the present invention.

That is, the present invention relates to a 2-acylaminopropanol compound represented by the formula (I):

$$R^1-CH-CH-CH_2-R^2 \quad (I)$$
$$\overset{|}{OH} \quad \overset{|}{NHCOCH(CH_2)_mCH_3}$$
$$\overset{|}{R^{11}}$$

(wherein $R^1$ represents a phenyl group which may be substituted by 1 to 3 same or different substituents selected from alkyl, alkoxy, hydroxyl, hydroxyalkyl and nitro, $R^2$ represents the following formula (II), (III), (IV), (V) or (VI)

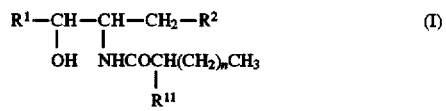

(II)

(III)

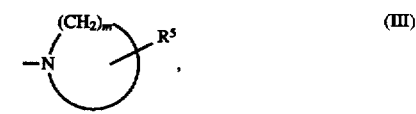

(IV)

(V)

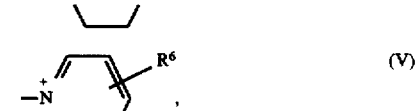

(VI)

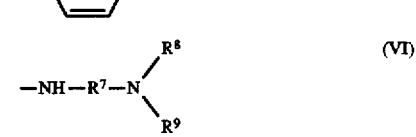

(wherein $R^3$ and $R^4$ are the same or different and each represent a hydrogen atom, an alkyl group having 1 to 6 carbon atoms, an alkenyl group, a hydroxyalkyl group, an alkoxyalkyl group, an aminoalkyl group, a cycloalkyl group, a hydroxycycloalkyl group, an aralkyl group or a piperazino group which may be substituted by an alkyl group, $R^5$ represents 1 or 2 or more same or different substituents selected from a hydrogen atom, a hydroxyl group, a lower alkyl group, an alkoxy group, a hydroxyalkyl group, a carboxyl group, an alkoxycarbonyl group, an aralkyl group, a piperidino group, an acyloxy group, an amino group and an aminoalkyl group, $R^6$ represents a hydrogen atom or 1 or 2 or more same or different substituents which are the same as $R^5$, $R^7$ represents an alkylene group which may be interrupted by oxygen, $R^8$ and $R^9$ are the same or different and each represent a hydrogen atom, a lower alkyl group or a hydroxy-lower alkyl group, or $R^8$ and $R^9$ represent, together with a nitrogen atom to which they are bonded, a piperidino group or morpholino group which may be substituted by a lower alkyl, m represents an integer of 2 to 6, p represents 2 or 3, X represents the following formula (VII) or (VIII),

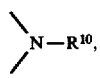 (VII)

 (VIII)

in the formula (VII), $R^{10}$ represents a hydrogen atom, a lower alkyl group, an acyl group, a lower alkoxycarbonyl group or a pyridyl group) $R^{11}$ represents a hydrogen atom or a hydroxyl group, and n represents an integer of 3 to 15) or a pharmaceutically acceptable salt thereof. Also, the present invention relates to a medical composition, particularly an antiviral agent or an agent for treating neuronal diseases, which comprises the 2-acylaminopropanol compound represented by the above formula (I) or a pharmaceutically acceptable salt thereof as an active ingredient.

Also, the present invention relates to a method for treating viral infectious diseases, which comprises administering the 2-acylaminopropanol compound represented by the above formula (I) or a pharmaceutically acceptable salt thereof in an effective amount for inhibiting growth of viruses to mammals which are infected with viruses.

Also, the present invention relates to a method for treating neuronal diseases, which comprises administering the 2-acylaminopropanol compound represented by the above formula (I) or a pharmaceutically acceptable salt thereof in an effective amount for accelerating biosynthesis of glycosphingolipids, accelerating neurite extension and/or accelerating synapse formation to mammals which suffer from neuronal diseases caused by disorders of peripheral nervous system or central nervous system.

Also, the present invention relates to use of the 2-acylaminopropanol compound represented by the above formula (I), a pharmaceutically acceptable salt thereof or a medical composition which comprises either of them, for preparing an antiviral agent.

Further, the present invention relates to use of the 2-acylaminopropanol compound represented by the above formula (I), a pharmaceutically acceptable salt thereof or a medical composition which comprises either of them, for preparing an agent for treating neuronal diseases caused by disorders of peripheral nervous system or central nervous system.

BEST MODE FOR PRACTICING THE INVENTION

Figure 1A:
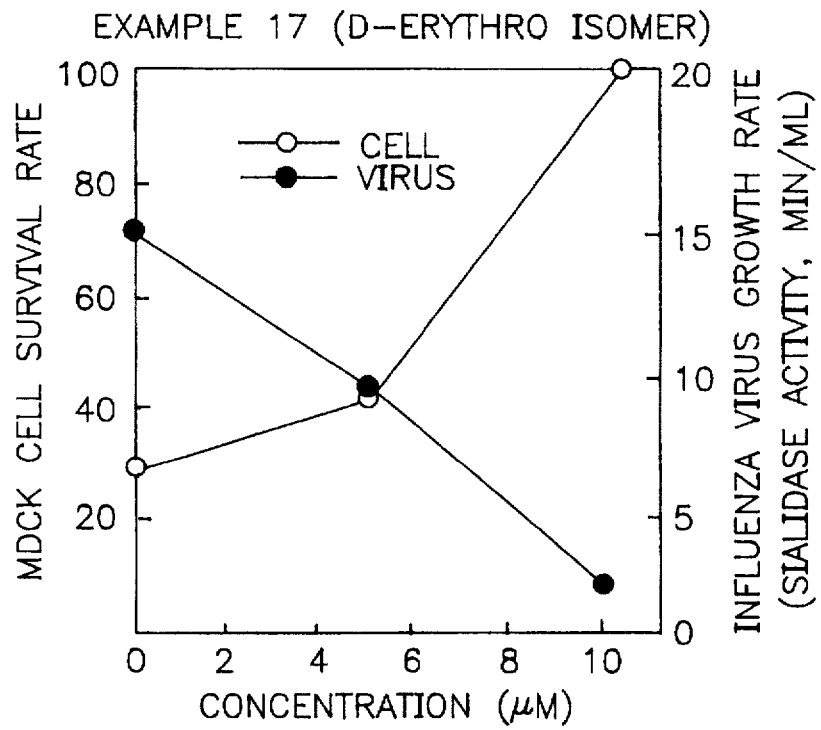
FIGS. 1 to 3 are views showing antiviral activities to influenza virus, using compounds of Examples 16, 17, 19 and 20.

In the following, the present invention is described particularly.

In the above formula, the carbon number of the alkyl, alkoxy or hydroxyalkyl group as a substituent of the phenyl group of $R^1$ is preferably 1 to 4. It may be specifically exemplified by methyl, ethyl, propyl, methoxy, ethoxy, hydroxymethyl, etc.

When $R^2$ represents the formula (II), the alkyl group having 1 to 6 carbon atoms of $R^3$ and $R^4$ may be exemplified by a straight or branched alkyl group such as methyl, ethyl, propyl, isopropyl, butyl, isobutyl, heptyl and hexyl; the alkenyl group may be exemplified by an alkenyl group having 3 to 4 carbon atoms such as allyl, 1-propenyl and 2-butenyl; the hydroxyalkyl group may be exemplified by hydroxyethyl; the alkoxyalkyl group may be exemplified by an alkoxyalkyl group having 3 to 6 carbon atoms such as methoxyethyl and ethoxyethyl; the aminoalkyl group may be exemplified by aminoethyl; the cycloalkyl group may be exemplified by a cycloalkyl group having 5 to 8 carbon atoms such as cyclopentyl and cyclohexyl; the hydroxycycloalkyl group may be exemplified by one in which the above cycloalkyl group is substituted by a hydroxyl group, such as 4-hydroxycyclohexyl; the aralkyl group may be exemplified by a phenylalkyl group having 7 to 9 carbon atoms such as benzyl and α-methylbenzyl; and the piperazino group which may be substituted by an alkyl group may be exemplified by piperazino and 4-methylpiperazino and (N-methyl-piperazino). A preferred group of the formula (II) is amino; a mono- or di-lower alkylamino group such as methylamino, ethylamino, isopropylamino, isobutylamino, dimethylamino, diethylamino, dipropylamino and methyl (ethyl) amino; 2-hydroxyethylamino and bis(2-hydroxyethyl)amino(diethanolamino); 2-aminoethylamino; cyclohexylamino and 4-hydroxycyclohexylamino; benzylamino and α-methylbenzylamino.

When $R^2$ represents the formula (III), the lower alkyl group of $R^5$ may be exemplified by an alkyl group having 1 to 4 carbon atoms such as methyl and ethyl; the alkoxy group may be exemplified by methoxy and ethoxy; the hydroxyalkyl group may be exemplified by hydroxymethyl and 2-hydroxyethyl; the alkoxycarbonyl group may be exemplified by methoxycarbonyl and ethoxycarbonyl; the aralkyl group may be exemplified by benzyl; the acyloxy group may be exemplified by acetoxy; and the aminoalkyl group may be exemplified by an aminomethyl group. A preferred group of the formula (III) may be exemplified by ethyleneimino, azetidino, pyrrolidino, piperidino, azepino, 2- or 3-hydroxypyrrolidino, 2-hydroxymethylpyrrolidino, 2-, 3- or 4-hydroxypiperidino, 3,4-dihydroxypiperidino, 3,4,5-trihydroxypiperidino, 2-, 3- or 4-hydroxymethylpiperidino, 2-, 3- or 4-hydroxyethylpiperidino, 2-, 3- or 4-methylpiperidino, 3,5-dimethylpiperidino, 3-hydroxymethyl-4,5-dihydroxypiperidino, 2-hydroxymethyl-3,4,5-trihydroxypiperidino, 4-methoxypiperidino, 4-methoxycarbonylpiperidino, 4-carboxypiperidino, 4-ethoxycarbonylpiperidino, 4-benzylpiperidino, 4-piperidinopiperidino, etc.

When $R^2$ represents the formula (IV), it may be exemplified by thiomorpholino, piperazino, N-methylpiperazino, N-methoxycarbonylpiperazino, N-ethoxycarbonylpiperazino, N-(2-pyridyl)piperazino, N-formylpiperazino, N-acetylpiperazino, N-methyl-1,4-diazacycloheptane-1-yl, etc.

When $R^2$ represents the formula (V), the substituent of $R^6$ may be exemplified by those which are the same as $R^5$, and it is a pyridinium quaternary base which may have these substituents.

When $R^2$ represents the formula (VI), the alkylene group which may be interrupted by oxygen, represented by $R^7$ may be exemplified by ethylene, trimethylene and —$(CH_2)_q$—O—$(CH_2)_r$— (where q and r each represent 2 or 3); the lower alkyl group of $R^8$ and $R^9$ may be exemplified by an alkyl group having 1 to 4 carbon atoms such as methyl, ethyl, propyl, butyl, etc.; the hydroxy-lower alkyl group may be exemplified by 2-hydroxyethyl; and when $R^8$ and $R^9$ are a piperidino group which may be substituted by a lower alkyl, together with a nitrogen atom to which they are bonded, they may be exemplified by piperidino and 2-, 3- or 4-methylpiperidino. A preferred group of the formula (VI) may be exemplified by 2-(dimethylamino)ethylamino, 2-(methylamino)ethylamino, 2-(diethylamino)ethylamino, 2-(ethylamino)ethylamino, 3-(dimethylamino)propylamino, 3-(diethylamino)propylamino, 3-(dibutylamino) propylamino, 3-bis(2-hydroxyethyl)amino)propylamino, 2-piperidinoethylamino, 2-(4-methylpiperidino)ethylamino, 3-piperidinopropylamino, 3-(2-methylpiperidino) propylamino, 3-(4-methylpiperidino)propylamino, 2-morpholinoethylamino, 3-morpholinopropylamino, etc.

In the above formula (VII), the lower alkyl group represented by $R^{10}$ may be exemplified by an alkyl group having 1 to 4 carbon atoms such as methyl, ethyl, propyl, butyl, etc.; the acyl group may be exemplified by an aliphatic acyl group such as formyl, acetyl, propionyl, butyryl, valeryl, palmitoyl, stearoyl, oleoyl, etc., and an aromatic acyl group such as benzoyl, toluoyl, salicyloyl, cinnamoyl, naphthoyl, phthaloyl, etc., and others; and the lower alkoxycarbonyl group may be exemplified by a carbonyl group having an alkoxy group with 1 to 4 carbon atoms, such as methoxycarbonyl, ethoxycarbonyl, propoxycarbonyl, butoxycarbonyl, etc.

Among the compounds represented by the above formula (I), from the comprehensive standpoints such as availability of a starting material, economy, easiness of synthesis, etc., preferred are compounds in which $R^1$ is a phenyl group which may be substituted by 1 to 2 same or different substituents selected from a hydroxyl group and a methoxy group, $R^2$ is the formula (II), (III) or (IV);

in the formula (II), $R^3$ and $R^4$ are the same alkyl groups having 1 to 3 carbon atoms: or $R^3$ is a hydrogen atom; and $R^4$ is a cycloalkyl group or hydroxycycloalkyl group having 5 to 6 carbon atoms; more preferably a dimethylamino group, a diethylamino group, a cyclohexylamino group or a 4-hydroxycyclohexylamino group;

in the formula (III), it is a pyrrolidino group, 3-hydroxypyrrolidino group, piperidino group or 4-hydroxypiperidino group in which $R^5$ is a hydrogen atom or a hydroxyl group; and m is 4 or 5;

in the formula (IV), it is a N-methylpiperazino group in which p is 2; X is the formula (VII); and $R^{10}$ is a methyl group;

$R^{11}$ is a hydrogen atom, and n is an integer of 5 to 13.

Among the compounds represented by the above formula (I), most preferred are compounds in which $R^1$ is a phenyl group, $R^{11}$ is a hydrogen atom, n is 5 to 13, $R^2$ is a diethylamino group, a 4-hydroxypiperidino group, a N-methylpiperazino group or a 3-hydroxypyrrolidino group.

In the compound of the formula (I), 4 stereoisomers of a D-threo isomer (1R, 2R), a L-threo isomer (1S, 2S), a D-erythro isomer (1S, 2R) and a L-erythro isomer (1R, 2S) exist, and among them, erythro isomers (D-, DL- and L-isomers) having a steric configuration similar to that of natural ceramides are preferred from the points that it is estimated that they compete specifically with a glycolipid receptor of host cell membranes having ability of binding to viruses, they show a tendency that an antiviral activity is stronger than that of threo isomers, and toxicity is low.

Among the compounds represented by the above formula (I), as a compound preferred from the standpoint of biological and pharmacological actions, there may be mentioned the following ones. That is, from the point of an antiviral action, it is preferred that $R^1$ is a phenyl group which may be substituted by 1 to 2 hydroxyl groups or methoxy groups; $R^2$ is a dimethylamino group, a diethylamino group, a dipropylamino group, a piperidino group, a 4-hydroxypiperidino group or a 2-hydroxymethylpiperidino group; $R^{11}$ is a hydrogen atom or a hydroxyl group; and n is an integer of 5 to 13, and it is a D-erythro isomer (1S, 2R) or a L-erythro isomer (1R, 2S), and more preferably, there may be mentioned one in which $R^1$ is a phenyl group; $R^2$ is a diethylamino group or a 4-hydroxypiperidino group; $R^{11}$ is a hydrogen atom; n is an integer of 7 to 13, and it is a D-erythro isomer (1S, 2R).

Also, as a compound which accelerates biosynthesis of glycosphingolipids, and has possible therapeutic use to neuronal diseases of which is described, it is preferred that $R^1$ is a phenyl group which may be substituted by 1 to 2 hydroxyl groups or methoxy groups; $R^2$ is a 4-hydroxycyclohexylamino group, a 3-hydroxypyrrolidino group, a 4-hydroxypiperidino group, a 3,4-dihydroxypiperidino group, a 3,4,5-trihydroxypiperidino group, a 3-hydroxymethyl-4,5-dihydroxypiperidino group or a N-methylpiperazino group; $R^{11}$ is a hydrogen atom or a hydroxyl group; and n is an integer of 5 to 13, and it is a L-threo isomer (1S, 2S), a D-erythro isomer (1S, 2R) or a L-erythro isomer (1R, 2S), and more preferably, there may be mentioned one in which $R^1$ is a phenyl group; $R^2$ is a 4-hydroxycyclohexylamino group, a 3-hydroxypyrrolidino group, a 4-hydroxypiperidino group or a N-methylpiperazino group; $R^{11}$ is a hydrogen atom; n is an integer of 5 to 13, and it is a L-threo isomer (1S, 2S).

Further, as a compound which inhibits biosynthesis of glycosphingolipids, and no possible therapeutic use to cancer of which is described, it is preferred that $R^1$ is a phenyl group which may be substituted by 1 to 2 hydroxyl groups or methoxy groups; $R^2$ is a cyclohexylamino group, a pyrrolidino group or a piperidino group; $R^{11}$ is a hydrogen atom or a hydroxyl group; and n is an integer of 5 to 13, and it is a D-threo isomer (1R, 2R), and more preferably, there may be mentioned one in which $R^1$ is a phenyl group; $R^2$ is a cyclohexylamino group, a pyrrolidino group or a piperidino group; $R^{11}$ is a hydrogen atom; n is an integer of 7 to 13, and it is a D-threo isomer (1R, 2R).

The compound represented by the above formula (I) can be synthesized by, for example, the following method described in J. Lipid. Res., Vol. 28, 565–571 (1987) and J. Biochem., Vol. 111, 191–196 (1992).

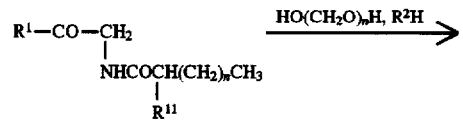

-continued

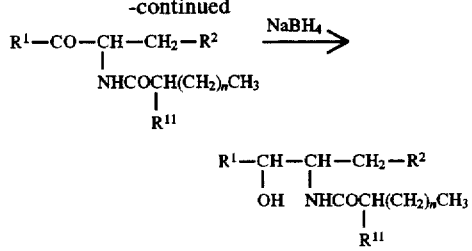

wherein HO(CH$_2$O)$_n$H represents paraformaldehyde.

A mixture of the resulting 4 isomers can be separated by fractional crystallization using chloroform/ether to obtain a DL-threo isomer and a DL-erythro isomer, respectively.

Also, the compound represented by the above formula (I) can be synthesized as a compound having a desired steric configuration relative to the respective optically active carbon atoms to which a hydroxy group and an amino group of a 2-acylaminopropanol skeleton are bonded, by using a chiral compound as a starting material as shown below and carrying out the following reactions.

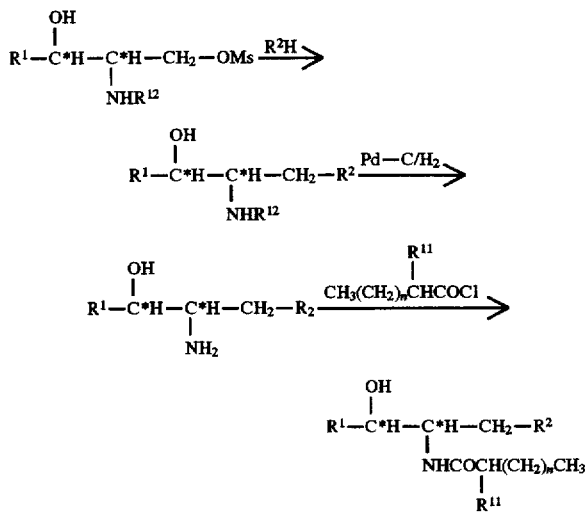

wherein * represents asymmetric carbon; $R^{12}$ is a protective group for an amino group, and there may be mentioned, for example, a benzyloxycarbonyl group, a t-butyloxycarbonyl group, a benzenesulfonyl group, a fluorenylmethyloxycarbonyl group, etc.; and Ms represents a methanesulfonyl group.

As a pharmaceutically acceptable salt of the compound represented by the above formula (I), there may be mentioned a salt of an inorganic acid such as hydrochloric acid, phosphoric acid, sulfuric acid, nitric acid, formic acid, etc.; and a salt of an organic acid such as acetic acid, citric acid, lactic acid, malic acid, oxalic acid, maleic acid, fumaric acid, succinic acid, trifluoroacetic acid, methanesulfonic acid, p-toluenesulfonic acid, etc.

Pharmaceutical Preparation

The antiviral agent of the present invention containing the 2-acylaminopropanol compound represented by the formula (I) or a pharmaceutically acceptable salt thereof can be used for preventing or treating infectious diseases of mammals including human by various viruses, for example, the following viruses:

influenza virus (Influenza virus (hereinafter abbreviated to "V.")),

RS virus (Respiratory syncytial V.),
parainfluenza virus (Parainfluenza V.),
Rhinovirus (Rhinovirus),
coxsackievirus (Coxsackie V.)
echovirus (Echo V.),
adenovirus (Adenovirus),
herpes simplex virus (Herpes simplex V.),
Varicella zoster virus (Herpes zoster V.),
cytomegalovirus (Cytomegalovirus),
Epstein-Barr virus (Epstein-Barr V.),
herpes virus hominis (Herpesvirus hominis),
human immunodeficiency virus (Human immunodeficiency V.),
hepatitis B virus (Hepatitis B V.),
hepatitis C virus (Hepatitis C V.),
Lassa virus (Lassa fever V.),
Marburg fever virus (Marburg V.),
Hanttan virus (Korean hemorrhagic fever V.),
mumps virus (Mumps V.),
Sendai virus (Sendai V.),
rabies virus (Lyssavirus, rabies V.),
rotavirus (Rotavirus),
Reovirus (Reovirus),
human T cell leukemia virus (Human T cell leukemia V.), etc.

By administering an effective amount of the 2-acylaminopropanol compound represented by the formula (I) or a pharmaceutically acceptable salt thereof to mammals including human which suffer from neuronal diseases caused by disorders of peripheral nervous system or central nervous system, said animals can be treated. As a representative disease, there may be mentioned various central nervous system diseases which are expected to be treated by regenerating nerve fibers, for example, apoplexy, cerebral infarction, cerebral hemorrhage, cerebral injury, dysmnesia, senile dementia, Alzheimer's disease, parkinsonism, etc.; and various peripheral nervous system diseases, for example, polyneuropathy caused by cacochymia, mechanical neuropathy, toxic neuropathy, etc.

PDMP which is a 2-acylaminopropanol compound can pass a blood-brain barrier (J. Lipid Res., Vol. 32, 713–722 (1991)) so that effectiveness to cerebral neuronal diseases as an injection and an oral agent can be expected. In particular, it is estimated that a liposome preparation having a fine size such as lipid superfine particles (lipid nanosphere), etc. or a lipid emulsion preparation on which the 2-acylaminopropanol compound is carried can pass a blood-brain barrier by about 10 times as compared with physiological saline so that it is effective when the preparation of the 2-acylaminopropanol compound of the present invention or a pharmaceutically acceptable salt thereof is used for treating cerebral neuronal diseases.

The medical composition of the present invention can be used for preventing or treating various viral infectious diseases and as an agent for treating neuronal diseases and an antitumor agent for mammals including human. A pharmaceutical preparation to be administered orally or parenterally can be obtained by using the compound represented by the above formula (I) or a salt thereof with a carrier, an excipient and other additives.

As an oral preparation, there may be mentioned a solid preparation such as a powder, a granule, a capsule, a tablet, etc.; and a liquid preparation such as a syrup, an elixir, an emulsion, etc. The powder can be obtained by, for example, mixing with an excipient such as lactose, starch, crystalline cellulose, calcium lactate, calcium hydrogen phosphate, magnesium aluminometasilicate, silicic acid anhydride, etc. The granule can be obtained by adding the above excipient and, if necessary, for example, a binder such as saccharose, hydroxypropyl cellulose, polyvinylpyrrolidone, etc. or a disintegrator such as carboxymethyl cellulose, calcium carboxymethyl cellulose, etc. and granulating the mixture by a wet method or a dry method. The tablet can be obtained by tableting the above powder or granule as such or with a lubricant such as magnesium stearate, talc, etc. Further, the above tablet or granule can be made an enteric or prolonged action preparation by covering it with an enteric base such as hydroxypropylmethylcellulose phthalate, a methyl methacrylate copolymer, etc. or covering it with ethyl cellulose, carnauba wax, hardened oil, etc. A hard capsule can be obtained by filling a hard capsule with the above powder or granule. Further, a soft capsule can be obtained by dissolving the compound represented by the above formula or a salt thereof in glycerin, polyethylene glycol, sesame oil, olive oil, etc. and covering the mixture with a gelatin film. The syrup can be obtained by dissolving a sweetener such as saccharose, sorbitol, glycerin, etc. and the compound represented by the above formula or a salt thereof in water. In addition to the sweetener and water, essential oil, ethanol, etc. may be added to prepare an elixir, or gum Arabic, tragacanth, polysorbate 80, sodium carboxymethyl cellulose, etc. may be added to prepare an emulsion or a suspension. Further, a taste-modifying agent, a coloring agent, a preservative, etc. may be added to these liquid preparations, if necessary.

As a parenteral preparation, there may be mentioned an injection, an intrarectal administration agent, a pessary, an endermic agent, an inhalant, an aerosol, an ophthalmic agent, etc. The injection can be obtained by adding a pH-adjusting agent such as hydrochloric acid, sodium hydroxide, lactic acid, sodium lactate, sodium monohydrogen phosphate, sodium dihydrogen phosphate, etc.; an isotonizing agent such as sodium chloride, glucose, etc.; and distilled water for injection to the compound represented by the above formula or a salt thereof, sterilizing the mixture by filtration and then filling an ampoule with the mixture. Further, an injection which is dissolved when it is used can be obtained by adding mannitol, dextrin, cyclodextrin, gelatin, etc. and lyophilizing the mixture under vacuum. Also, an emulsion for injection can be made by adding an emulsifier such as lecithin, polysorbate 80, polyoxyethylene hardened castor oil, etc. to the compound represented by the above formula or a salt thereof and then emulsifying the mixture in water.

Further, as an injection, there may be mentioned a liposome preparation which enables improvements of solubility and a transition rate to a target organ. In particular, nanosphere-liposome (lipid superfine particles) can not only heighten a concentration in blood without being taken into reticuloendothelial system and lower a minimum effective dose required for exhibiting a pharmaceutical effect, but also pass a blood-brain barrier easily so that it is suitable when it is used for treating cerebral neuronal diseases. The liposome preparation can be prepared according to a known liposome preparation method (C. G. Knight, Liposomes: From Physical Structure to Therapeutic Applications, pp. 51–82, Elsevier, Amsterdam (1981); Proc. Natl. Acad. Sci., U.S.A., Vol. 75, 4194 (1978)).

That is, as an amphipathic substance forming a liposome membrane, there may be used a phospholipid such as a natural phospholipid (yolk lecithin, soybean lecithin, sphingomyelin, phosphatidylserine, phosphatidylglycerol, phosphatidylinositol, diphosphatidylglycerol, phosphatidylethanolamine, cardiolipin, etc.), a synthetic phospholipid (distearoyl phosphatidylcholine, dipalmitoyl phosphatidylcholine, dipalmitoyl phosphatidylethanolamine, etc.) and others. Further, in order to improve membrane stability, fluidity and membrane permeability of the medicine, there may be used known various additives such as cholesterols (cholesterol, ergosterol, phytosterol, sito-sterol, stigmasterol, etc.), a substance which is known to impart negative charge to liposome (phosphatidic acid, dicetyl phosphate, etc.), a substance which is known to impart positive charge (stearylamine, stearylamine acetate, etc.), an antioxidant (tocopherol, etc.), an oily substance (soybean oil, cottonseed oil, sesame oil, cod-liver oil, etc.) and others.

Preparation of liposome can be carried out by, for example, the following method. The above amphipathic substance and additives, and the compound of the present invention are dissolved in an organic solvent (chloroform, dichloromethane, ethanol, methanol, hexane, etc. alone or a mixed solvent thereof), respectively, both solutions are mixed, the organic solvent is removed in a vessel such as a flask, etc. in the presence of an inert gas (a nitrogen gas, an argon gas, etc.), and a thin membrane is attached to a vessel wall. Then, this thin membrane is added to a suitable aqueous medium (physiological saline, a buffer, a phosphate buffered physiological saline, etc.), and the mixture is stirred by a stirrer. In order to obtain liposome having a small particle size, the mixture is further dispersed by using an ultrasonic emulsifier, a pressurization type emulsifier, a French press cell pulverizer, etc. As described above, preparation of liposome proceeds by treating, with a membrane filter, a liquid in which the amphipathic substance, etc. required for preparation of liposome and the compound of the present invention are dispersed in the aqueous medium to obtain nanosphere liposome (lipid nanosphere; a particle size of about 25 to 50 nm) in which a particle size distribution is controlled. Further, liposome may be subjected to fractionation treatment such as ultrafiltration, centrifugation, gel filtration, etc. to remove the medicine which is not carried.

Further, by making the compound of the present invention to be carried on liposome having, on a membrane thereof, a glucose residue, a tyrosine residue, a mannose residue or sulfatide obtained by adding β-octylglucoside, L-tyrosin-7-amido-4-methylcoumarin, phenylaminomannoside or sulfatide as a membrane-forming substance in addition to the above amphipathic substance and additives, the liposome can be made to pass a blood-brain barrier easily (as to a method itself, see Japanese Provisional Patent Publication No. 69332/1992).

The intrarectal administration agent can be obtained by adding a base for a suppository such as mono-, di- or triglyceride of cacao aliphatic acid, polyethylene glycol, etc. to the compound represented by the above formula (I) or a salt thereof, then melting the mixture by heating, pouring it into a mold and cooling it, or dissolving the compound represented by the above formula (I) or a salt thereof in polyethylene glycol, soybean oil, etc. and then covering the mixture with a gelatin film. The endermic agent can be obtained by adding white petrolatum, beeswax, liquid paraffin, polyethylene glycol, etc. to the compound represented by the above formula (I) or a salt thereof, heating the mixture, if necessary, and kneading it. A tape agent can be obtained by kneading the compound represented by the above formula (I) or a salt thereof with an adhesive such as rosin, an alkyl acrylate polymer, etc. and spreading the mixture on unwoven fabric, etc. The inhalation can be obtained by, for example, dissolving or dispersing the compound represented by the above formula (I) or a salt thereof in a propellant such a pharmaceutically acceptable inert gas, etc. and filling a pressure container with the mixture.

Administration Method

The administration method of a medicine containing the compound represented by the above formula (I) of the present invention or a salt thereof as an effective ingredient is not particularly limited, but when it is used as an antiviral agent, injection such as intramuscular injection, intravenous injection, hypodermic injection, etc., inhalation, intranasal administration, oral administration or external use is preferred, and when it is used for treating neuronal diseases caused by disorders of central nervous system, intramuscular injection, intravenous injection, hypodermic injection or intraperitoneal injection is preferred. Particularly when it is used for treating cerebral neuronal diseases, a method of injecting the liposome preparation or the lipid emulsion preparation is preferred.

Dose

The dose may be suitably determined depending on a target disease, age, health condition, weight, etc. of a patient, but it is generally 0.25 to 200 mg/kg, preferably 0.5 to 100 mg/kg by one dose or divided doses per day.

Toxicity

Almost no or no cytotoxicity of the compound represented by the formula (I) of the present invention or a salt thereof was observed in a dose by which a biological activity as a medicine was exhibited.

In particular, 10 µM of DL-erythro-2-decanoylamino-3-(4-hydroxypiperidino)-1-phenyl-1-propanol completely suppressed growth of influenza virus with which MDCK cells were infected, but cytotoxicity at this concentration was not observed at all.

Utilizability in Industry

According to the present invention, a novel 2-acylaminopropanol compound having a nitrogen-containing substituent, which is useful as an antiviral agent and a neuronal diseases-treating agent to various diseases caused by disorders of central nervous system or peripheral nervous system having a strong activity as compared with PDMP can be provided. Also, the compound of the present invention, particularly a D-threo isomer specifically inhibits biosynthesis of glycolipids so that growth of cancer cells is suppressed and use for treating cancers is expected.

EXAMPLES

In the following, Examples of the present invention are shown, but the present invention is not limited thereby.

Example 1.

Synthesis of 2-decanoylamino-1-phenyl-3-piperidino-1-propanol a) Paraformaldehyde (168.0 mg, 5.54 mmol) and piperidine (947.4 µl, 9.58 mmol) were added to a 95% ethanol solution (10 ml) containing N-decanoyl-2-aminoacetophenone (2.0 g, 6.91 mmol), and the mixture was refluxed overnight. After the solvent was removed by evaporation, the residue was dissolved in 75% ethanol (10 ml), and under ice cooling, a 75% ethanol solution (10 ml) containing sodium borohydride (960 mg, 25.4 mmol) was added dropwise to the solution. After completion of the reaction, the pH of the reaction mixture was adjusted to 4 with 1N-hydrochloric acid, and the mixture was extracted with chloroform. The organic layer was washed with a saturated brine, dried over anhydrous sodium sulfate and then filtered, and the solvent was removed by evaporation. After chloroform was added to this residue to prepare a 25% (w/v) solution, ether was added to the solution so that chloroform : ether became 1:3. After the mixture was stirred at 4° C. overnight, precipitated crystals (a DL-threo isomer, 180.5 mg) were collected by filtration.

TLC Rf 0.36 (CHCl$_3$: MeOH:ACOH=9:1:1) $^1$H-NMR (CDCl$_3$): 7.37–7.23 (5H, m, aromatic), 5.88 (1H, d, J=7.3Hz, NH), 4.96 (1H, d, J=3.6Hz, H-1), 4.30 (1H, m, H-2), 2.64-2.45 (6H, m, CH$_2$N(CH$_2$)$_2$), 2.09 (2H, m, COCH$_2$), 1.63 (4H, m, H-3', H-5'), 1.55-1.45 (4H, m, COCH$_2$CH$_2$, H-4'), 1.24 (12H, brs, (CH$_2$)$_6$CH$_3$), 0.88 (3H, t, CH$_3$) MS (FAB) 389 (M+H)$^+$ b) Ether was further added to the filtrate of the stage a) so that chloroform:ether became 1:5, and the same operation was carried out to obtain second crystals (a DL-erythro isomer, 154.5 mg).

TLC Rf 0.44 (CHCl$_3$:MeOH:AcOH=9:1:1) $^1$H-NMR (CDCl$_3$): 7.37-7.22 (5H, m, aromatic), 5.93 (1H, d, J=6.6Hz, NH), 4.78 (1H, d, J=5.3Hz, H-1), 4.22 (1H, m, H-2), 2.62-2.45 (6H, m, CH$_2$N(CH$_2$)$_2$), 2.10 (2H, m, COCH$_2$), 1.58 (4H, m, H-3', H-5'), 1.51-1.44 (4H, m, COCH$_2$CH$_2$, H-4'), 1.23 (12H, brs, (CH$_2$)$_6$CH$_3$), 0.88 (3H, t, CH$_3$) MS (FAB) 389 (M+H)$^+$ Example 2

Synthesis of 2-decanoylamino-3-(4-hydroxypiperidino)-1-phenyl-1-propanol

Paraformaldehyde (168.0 mg, 5.54 mmol) and 4-hydroxypiperidine (969.0 mg, 9.58 mmol) were added to a 95% ethanol solution (10 ml) containing N-decanoyl-2-amino-acetophenone (2.0 g, 6.91 mmol), and the mixture was refluxed overnight. After the solvent was removed by evaporation, the residue was dissolved in 75% ethanol (10 ml), and under ice cooling, a 75% ethanol solution (10 ml) containing sodium borohydride (960 mg, 25.4 mmol) was added dropwise to the solution. After completion of the reaction, the solvent was removed by evaporation, and the residue was neutralized with 1N-hydrochloric acid. This aqueous solution was extracted with ethyl acetate, the organic layer was washed with a saturated brine, dried over anhydrous sodium sulfate and then filtered, and the solvent was removed by evaporation. The reaction residue was purified by silica gel column chromatography (CHCl$_3$: MeOH:H$_2$O=9:1:0.1) to obtain a mixture (1.07 g) of 4 kinds of stereoisomers. 85 mg of the product purified by silica gel column chromatography was further separated by preparative thin layer chromatography (TLC) (Merck Art 5744, 20 mm×20 mm, 4 plates); CHCl$_3$:MeOH:AcOH=9:1:1 to obtain a white solid (6.5 mg of a DL-erythro isomer and 13.9 mg of a DL-threo isomer).

[DL-erythro isomer] TLC Rf 0.24 (CHCl$_3$:MeOH:AcOH=9:1:1) $^1$H-NMR (CDCl$_3$): 7.36-7.26 (5H, m, aromatic), 6.29 (1H, d, J=4.3Hz, NH), 4.83 (1H, d, J=5.0Hz, H-1), 4.25 (1H, m, H-2), 3.76 (1H, m, H-4'), 2.90-2.78 (2H, br, H-2'A), 2.70-2.56 (2H, m, H-3), 2.38-2.35 (2H, br, H-2'B), 2.01-1.91 (2H, br, H-3'A), 2.16-2.10 (2H, m, COCH$_2$), 1.67-1.57 (4H, m, H-3'B, COCH$_2$OH$_2$), 1.24 (12H, brs, (CH$_2$)$_6$CH$_3$), 0.88 (3H, t, CH$_3$) MS (FAB) 405 (M+H)$^+$

[DL-threo isomer] TLC Rf 0.20 (CHCl$_3$:MeOH:AcOH= 9:1:1) $^1$H-NMR (CDCl$_3$): 7.37-7.23 (5H, m, aromatic), 6.77 (1H, d, J=7.6Hz, NH), 4.95 (1H, d, J=3.6Hz, H-1), 4.41 (1H, m, H-2), 3.78 (1H, m, H-4'), 3.06-3.03 (2H, br, H-2'A), 2.86 (2H, m, H-3), 2.80-2.70 (2H, br, H-2'B), 2.10-2.00 (4H, m, H-3'A, COCH$_2$), 1.76 (2H, m, H-3'B), 1.45 (2H, m, COCH$_2$CH$_2$), 1.24 (12H, brs, (CH$_2$)$_6$CH$_3$), 0.88 (3H, t, CH$_3$) MS (FAB) 405 (M+H)$^+$ Example 3

Synthesis of 2-decanoylamino-3-diethylamino-1-phenyl-1-propanol

According to the method of Example 2, synthesis was carried out in the same manner by using diethylamine (991 μl, 9.60 mmol) in place of 4-hydroxypiperidine. The reaction residue was purified by silica gel column chromatography (CHCl$_3$:MeOH=20:1) to obtain a mixture (280.0 mg) of 4 kinds of stereoisomers. 50 mg of the product purified by silica gel column chromatography was further separated by preparative TLC (Merck Art 5744, 20 mm×20 mm, 2 plates); CHCl$_3$:MeOH:AcOH=95:5:10 to obtain a colorless oily product (4.6 mg of a DL-erythro isomer and 7.0 mg of a DL-threo isomer).

[DL-erythro isomer] TLC Rf 0.59 (CHC$_3$:MeOH:AcOH= 9:1:1), Rf 0.32 (CHCl$_3$:MeOH:AcOH=95:5:10) $^1$H-NMR (CDCl$_3$): 7.38-7.23 (5H, m, aromatic), 5.87 (1H, d, J=4.0 Hz, NH), 4.75 (1H, d, J=6.3Hz, H-1), 4.17 (1H, m, H-2), 2.97-2.50 (6H, m, CH$_2$N(CH$_2$)$_2$), 2.04 (2H, m, COCH$_2$), 1.45 (2H, COCH$_2$CH$_2$), 1.24 (12H, brs, (CH$_2$)$_6$CH$_3$), 1.05 (6H, brt, N (CH$_2$CH$_3$)$_2$, 0.88 (3H, t, (CH$_2$)$_6$CH$_3$) MS (FAB) 377 (M+H)$^+$

[DL-threo isomer] TLC Rf 0.53 (CHCl$_3$:MeOH:AcOH= 9:1:1), Rf 0.27 (CHCl$_3$:MeOH:AcOH=95:5:10) $^1$H-NMR (CDCl$_3$): 7.35-7.22 (5H, m, aromatic), 6.15 (1H, d, J=7.3Hz, NH), 5.01 (1H, d, J=3.3Hz, H-1), 4.21 (1H, m, H-2), 2.83-2.55 (6H, m, CH$_2$N(CH$_2$)$_2$), 2.07 (2H, m, COCH$_2$), 1.47 (2H, COCH$_2$CH$_2$), 1.23 (12H, brs, (CH$_2$)$_6$CH$_3$), 1.09 (6H, brt, N(CH$_2$CH$_3$)$_2$, 0.88 (3H, t, (CH$_2$)$_6$CH$_3$) MS (FAB) 377 (M+H)$^+$ Example 4

Synthesis of 2-decanoylamino-3-(2-(hydroxymethyl)-piperidino)-1-phenyl-1-propanol According to the method of Example 2, synthesis was carried out in the same manner by using 2-(hydroxymethyl)-piperidine (1.1 g, 9.58 mmol) in place of 4-hydroxypiperidine.

The reaction residue was purified by silica gel column chromatography (CHCl$_3$:MeOH:H$_2$O=9:1:0.05) to obtain a mixture (898.4 mg) of 8 kinds of stereoisomers. 72 mg of the product purified by silica gel column chromatography was further separated by preparative TLC (Merck Art 5744, 20 mm×20 mm, 4 plates); CHCl$_3$:MeOH:ACOH=9:1:1 to obtain a colorless oily product (7.5 mg).

TLC Rf 0.46 (CHCl$_3$:MeOH:AcOH=9:1:1) $^1$H-NMR (CDCl$_3$): 7.45-7.24 (5H, m, aromatic), 7.93 (1H, d, J=7.9Hz, NH), 5.05 (1H, d, J=4.6Hz, H-1), 4.36 (1H, m, H-2), 3.85-3.63 (2H, m, CH$_2$OH), 3.29-3.19 (4H, m, H-3, H-6'), 2.78 (1H, m, H-2'), 2.17 (2H, m, COCH$_2$), 1.62-1.51 (8H, m, H-3', H-4', H-5', COCH$_2$CH$_2$), 1.23 (12H, brs, (C$_2$H)$_6$CH$_3$), 0.88 (3H, t, CH$_3$) MS (FAB) 419 (M+H)$^+$ Example 5

Synthesis of 2-decanoylamino-3-(3-hydroxypiperidino)-1-phenyl-1-propanol

According to the method of Example 2, synthesis was carried out in the same manner by using 3-hydroxypiperidine (969 mg, 9.58 mmol) in place of 4-hydroxypiperidine. The reaction residue was purified by silica gel column chromatography (CHCl$_3$:MeOH:H$_2$O= 9:1:0.05 and then CHCl$_3$:MeOH:AcOH=9:1:1) to obtain a mixture (296.4 mg) of stereoisomers.

TLC Rf 0.27 (CHCl$_3$:MeOH:AcOH=9:1:1), 0.32 (CHCl$_3$:MeOH:1M—NH$_3$=9:1:0.1) $^1$H-NMR (CDCl$_3$): 7.37-7.23 (5H, m, aromatic), 6.44-6.32 (1H, m, NH), 4.98-4.89 (1H, m, H-1), 4.39-4.31 (1H, m, H-2), 3.91 (1H, m, H-3'), 2.86-2.55 (6H, m, CH$_2$N(CH$_2$)$_2$), 2.19-1.91 (4H, m, H-4'A, H-5'B, COCH$_2$), 1.75-1.42 (4H, m, H-4'B, H-5'B, COCH$_2$CH$_2$), 1.25 (12H, brs, (CH$_2$)$_6$CH$_3$), 0.88 (3H, t, CH$_3$) MS (FAB) 405 (M+H)$^+$ Example 6

Synthesis of 2-decanoylamino-1-phenyl-3-thiomorpholino-1-propanol

According to the method of Example 2, synthesis was carried out in the same manner by using thiomorpholine (987 mg, 9.58 mmol) in place of 4-hydroxypiperidine. The reaction residue was purified by silica gel column chromatography (CHCl$_3$:MeOH:H$_2$O=9:1:0.05) to obtain a mixture (903 mg) of 4 kinds of stereoisomers. 60 mg of the product purified by silica gel column chromatography was further separated by preparative TLC (Merck Art 5744, 20 mm×20 mm, 2 plates); CHCl$_3$:MeOH:AcOH=9:1:1 to obtain a colorless oily product (4.0 mg of a DL-erythro isomer and 2.5 mg of a DL-threo isomer).

[DL-erythro isomer] TLC Rf 0.62 (CHCl$_3$:MeOH:AcOH=9:1:1). $^1$H-NMR (CDCl$_3$): 7.36-7.27 (5H, m, aromatic), 6.80 (1H, d, J=6.9Hz, NH), 4.89 (1H, d, J=4.0 Hz, H-1), 4.33 (1H, m, H-2), 2.94-2.56 (10H, m, CH$_2$N(CH$_2$)$_2$, S(CH$_2$)$_2$), 2.14 (2H, m, COCH$_2$), 1.54 (2H, m, COCH$_2$CH$_2$) , 1.25 (12H, brs, (CH$_2$)$_6$CH$_3$), 0.88 (3H, t, CH$_3$) MS (FAB) 407 (M+H)$^+$

[DL-threo isomer] TLC Rf 0.55 (CHCl$_3$:MeOH:AcOH= 9:1:1) $^1$H-NMR (CDCl$_3$): 7.33-7.17 (5H, m, aromatic), 5.77 (1H, d, J=7.3Hz, NH), 4.87 (1H, d, J=3.6Hz, H-1), 4.19 (1H, m, H-2), 2.78-2.37 (1OH, m, CH$_2$N(CH$_2$)$_2$, S(CH$_2$)$_2$), 2.03 (2H, m, COCH$_2$), 1.43 (2H, m, COCH$_2$CH$_2$), 1.17 (12H, brs, (CH$_2$)$_6$CH$_3$), 0.81 (3H, t, CH$_3$) MS (FAB) 407 (M+H)$^+$ Example 7

Synthesis of 2-decanoylamino-3-(N-formylpiperazino)-1-phenyl-1-propanol

According to the method of Example 2, synthesis was carried out in the same manner by using N-formylpiperazine (1.22 g, 10.7 mmol) in place of 4-hydroxypiperidine to obtain the title substance (144.7 mg of a mixture of diastereomers at a (DL-erythro isomer:DL-threo isomer) ratio of 1:1) as a colorless oily product.

$^1$H-NMR (CDCl$_3$): 7.98 (1H, d, HCO), 7.37–7.25 (5H, m, aromatic), 5.90 (0 5H, d, J=7.9Hz, NH (a DL-erythro isomer)), 5.87 (0.5H, d, J=9.6Hz, NH (a DL-threo isomer)), 4.96 (0.5H, d, J=3.3Hz, H-1 (a DL-threo isomer)), 4.86 (0.5H, d, J=4.3Hz, H-1 (a DL-erythro isomer)), 4.27 (1H, m, H-2), 3.56-3.51 (2H, m, H-3'A, H-5'A), 3.39-3.32 (2H, m, H-3'B, H-5'B), 2.63-2.42 (6H, m, CH$_2$N(CH$_2$)$_2$), 2.15-2.07 (2H, m, CO—CH$_2$), 1.53-1.50 (2H, m, CO—CH$_2$—CH$_2$), 1.25 (12H, brs, (CH$_2$)$_6$—CH$_3$), 0.88 (3H, t, CH$_3$)

Example 8

Synthesis of (1S, 2S)-2-decanoylamino-3-(N-methylpiperazino)-1-phenyl-1-propanol (1S, 2S)-2-benzyloxycarbonylamino-1-phenyl-1,3-propanediol-3-methanesulfonyl ester (1.81 g, 4.78 mmol) was dissolved in ethanol, N-methylpiperazine (1.92 g, 19.2 mmol) was added thereto, and the mixture was stirred at 40° C. for 3 days. After completion of the reaction, the solvent was removed by evaporation under reduced pressure, a saturated sodium hydrogen carbonate solution was added to the residue, and the mixture was extracted with chloroform. The organic layer was dried over anhydrous sodium sulfate and then filtered, and the solvent was removed by evaporation. Next, the extract was dissolved in methanol, 10% palladium carbon was added thereto, and while the mixture was stirred vigorously, a hydrogen gas was introduced. After completion of the reaction, palladium carbon was removed by filtration, and the solvent was removed by evaporation under reduced pressure. Then, methanol was added to the reaction residue, and over ice bath, decanoyl chloride was added thereto in the presence of triethylamine. After completion of the reaction, the solvent was removed by evaporation under reduced pressure, a saturated sodium hydrogen carbonate solution was added thereto, and the mixture was extracted with chloroform. The organic layer was dried over anhydrous sodium sulfate and then filtered, and the solvent was removed by evaporation. Next, the extract was purified by silica gel column chromatography (chloroform:methanol=9:1) to obtain the title substance (10.0 mg) as a colorless oily product.

$^1$H-NMR (CDCl$_3$): 7.37-7.25 (5H, m, aromatic), 5.91 (1H, d, J=7.3Hz, NH), 4.95 (1H, d, J=3.4Hz, H-1), 4.29 (1H, m, H-2), 2.78-2.36 (10H, m, H-3, H-2', H-3', H-4', H-5'), 2.32 (3H, t, N-CH$_3$), 2.30-2.27 (1H, m, COCH$_2$(A)), 2.11-2.08 (1H, m, COCH$_2$(B)), 1.63-1.60 (1H, m, CO—CH$_2$—CH$_2$(A)), 1.53-1.48 (1H, m, CO—CH$_2$—CH$_2$(B)), 1.25 (12H, brs, (CH$_2$)$_6$—CH$_3$), 0.88 (3H, t, CH$_3$)

Example 9

Synthesis of (1S, 2S)-2-decanoylamino-3-((2S)-2-hydroxymethylpyrrolidino)-1-phenyl-1-propanol According to the method of Example 8, synthesis was carried out in the same manner by using (2S)-2-hydroxymethylpyrrolidine in place of N-methylpiperazine to obtain the title substance (89.6 mg) as a colorless oily product.

$^1$H-NMR (CDCl$_3$): 7.35-7.23 (5H, m, aromatic), 6.13 (1H, d, J=6.3Hz, NH), 4.99 (1H, d, J=3.4Hz, H-1), 4.14 (1H, m, H-2), 3.71-3.67 (1H, m, H-6'A), 3.57-3.53 (1H, m, H-6'B), 3.29-3.24 (1H, m, H-5'A), 3.14-3.09 (1H, m, H-3A), 2.83-2.78 (1H, m, H-3B), 2.76 (1H, m, H-2'), 2.38-2.32 (1H, m, H-5'B), 2.14-2.03 (2H, m, COCH$_2$), 1.92-1.83 (1H, m, H-3'A), 1.80-1.73 (2H, m, H-4'), 1.70-1.62 (1H, m, H-3'B), 1.50-1.43 (2H, m, COCH$_2$CH$_2$), 1.22 (12H, brs, (CH$_2$)$_6$CH$_3$), 0.88 (3H, t, CH$_3$)

Example 10

Synthesis of (1S, 2S)-2-decanoylamino-3-(3-hydroxypyrrolidino)-1-phenyl-1-propanol According to the method of Example 8, synthesis was carried out in the same manner by using 3-hydroxypyrrolidine in place of N-methylpiperazine to obtain the title substance (a mixture of diastereomers at a ratio of 1:1, 88.3 mg) as a colorless oily product.

$^1$H-NMR (CDCl$_3$): 7.36-7.24 (5H, m, aromatic), 5.91 (0.5H, d, J=7.3Hz, NH), 5.88 (0.5H, d, J=7.3Hz, NH), 5.0 (1H, H-1), 4.40 (1H, m, H-3'), 4.23 (1H, m, H-2), 3.06-3.01 (1H, m, H-5'A), 3.00-2.70 (3H, m, H-3, H-2'A), 2.67-2.63 (1H, m, H-2'B), 2.54-2.45 (1H, m, H-5'B), 2.21-2.12 (1H, m, H-4'A), 2.11-2.00 (2H, m, COCH$_2$), 1.79-1.74 (1H, m, H-4'B), 1.50-1.44 (2H, m, COCH$_2$CH$_2$), 1.22 (12H, brs, (CH$_2$)$_6$—CH$_3$), 0.88 (3H, t, CH$_3$)

Example 11

Synthesis of (1S, 2S)-2-decanoylamino-3-pyrrolidino-1-phenyl-1-propanol

According to the method of Example 8, synthesis was carried out in the same manner by using pyrrolidine in place of N-methylpiperazine to obtain the title substance (92.2 mg) as a colorless oily product.

$^1$H-NMR (CDCl$_3$): 7.36-7.23 (5H, m, aromatic), 5.91 (1H, d, J=7.8Hz, NH), 5.05 (1H, d, J=3.4Hz, H-1), 4.26 (1H, m, H-2), 2.86 (2H, d, J=5.4Hz, H-3), 2.70 (4H, m, H-2', H-5'), 2.07 (2H, m, COCH$_2$), 1.81 (4H, m, H-3', H-4'), 1.47 (2H, m, CO—CH$_2$—CH$_2$), 1.3-1.1 (12H, m, (CH$_2$)$_6$—CH$_3$), 0.88 (3H, t, CH$_3$)

Example 12

Synthesis of (1S, 2S)-2-decanoylamino-3-(3-hydroxymethylpiperidino)-1-phenyl-1-propanol According to the method of Example 8, synthesis was carried out in the same manner by using 3-hydroxymethylpiperidine in place of N-methylpiperazine to obtain the title substance (a mixture of diastereomers at a ratio of 1:1, 246.5 mg) as a colorless oily product.

$^1$H-NMR (CDCl$_3$): 7.36-7.24 (5H, m, aromatic), 5.96 (0.5H, d, J=7.8Hz, NH), 5.94 (0.5H, d, J=7.8Hz, NH), 4.96 (0.5H, d, J=3.4Hz, H-1), 4.94 (0.5H, d, J=3.4Hz, H-1), 4.33-4.26 (1H, m, H-2), 3.59-3.51 (1H, m), 3.50-3.42 (1H, m), 3.00-2.83 (2H, m), 2.59 (1H, dd, H-3A), 2.48 (1H, dd, H-3B), 2.3-2.0 (2H, m), 2.07 (2H, m, COCH$_2$), 1.9-1.5 (4H, m), 1.48 (2H, m, COCH$_2$—CH$_2$), 1.4-1.1 (12H, m, (CH$_2$)$_6$—CH$_3$), 1.10-1.00 (1H, m), 0.88 (3H, t, CH$_3$)

Example 13

Synthesis of (1S, 2S)-3-cyclohexylamino-2-decanoylamino-1-phenyl-1-propanol

According to the method of Example 8, synthesis was carried out in the same manner by using cyclohexylamine in place of N-methylpiperazine to obtain the title substance (40.6 mg) as a colorless oily product.

$^1$H-NMR (CDCl$_3$): 7.4-7.2 (5H, m, aromatic), 6.64 (1H, d, J=7.3Hz, NH), 5.14 (1H, d, J=2.5Hz, H-1), 4.37 (1H, m, H-2), 3.34 (1H, dd, J=4.9, 12.7Hz, H-3A), 3.13 (1H, dd, J=5.4, 16.3Hz, H-3B), 2.77 (1H, m, (CH$_2$)$_2$CHNH), 2.2-2.0 (4H, m), 1.76 (2H, d, J=12.7Hz), 1.63 (1H, d, J=10.7Hz), 1.5-1.0 (19H, m), 0.88 (3H, t, J=6.8Hz, CH$_3$)

Example 14

Synthesis of (1S, 2S)-2-decanoylamino-3-(4-hydroxycyclohexylamino)-1-phenyl-1-propanol According to the method of Example 8, synthesis was carried out in the same manner by using 4-hydroxycyclohexylamine in place of N-methylpiperazine to obtain the title substance (12.0 mg) as a colorless oily product.

$^1$H-NMR (CDCl$_3$): 7.4-7.2 (5H, m, aromatic), 6.36 (1H, d, J=6.8Hz, NH), 5.13 (1H, d, J=2.0Hz, H-1), 4.31 (1H, m, H-2), 3.61 (1H, m, CH$_2$CHOH), 3.34 (1H, dd, J=4.4, 12.7Hz, H-3A), 3.06 (1H, dd, J=4.9, 12.7Hz, H-3B), 2.73 (1H, m, CH$_2$CHNH), 2.2-1.9 (6H, m), 1.5-1.0 (18H, m), 0.88 (3H, t, J=6.8Hz, CH$_3$)

Example 15

Synthesis of (1S, 2S)-2-decanoylamino-3-(2-(N-morpholino)ethylamino)-1-phenyl-1-propanol According to the method of Example 8, synthesis was carried out in the same manner by using 2-(N-morpholino)ethylamine in place of N-methylpiperazine to obtain the title substance (91.7 mg) as a colorless oily product.

$^1$H-NMR (CDCl$_3$): 7.4-7.2 (5H, m, aromatic), 6.02 (1H, d, J=7.3Hz, NH), 4.64 (1H, d, J=2.4 Hz, H-1), 4.28 (1H, m, H-2), 3.80 (1H, dd, J=9.8, 14.2Hz), 3.68 (4H, t, J=4.4Hz, CH$_2$OCH$_2$), 3.50 (2H, m), 3.30 (1H, dd, J=5.9, 14.2Hz), 2.7-2.5 (2H, m), 2.48 (4H, t, J=4.4Hz, CH$_2$NCH$_2$), 2.4-2.3 (2H, m), 2.00 (2H, m, COCH$_2$), 1.65 (2H, m), 1.5-1.0 (14H, m, (CH$_2$)$_7$CH$_3$), 0.88 (3H, t, J=6.8Hz, CH$_3$)

Example 16

Synthesis of (1R, 2S)-2-decanoylamino-3-(4-hydroxypiperidino)-1-phenyl-1-propanol According to the method of Example 8, synthesis was carried out in the same manner by using (1R, 2S)-2-benzyloxycarbonylamino-1-phenyl-1,3-propanediol-3-methanesulfonyl ester in place of (1S, 2S)-2-benzyloxycarbonylamino-1-phenyl-1,3-propanediol-3-methanesulfonyl ester and using 4-hydroxypiperidine in place of N-methylpiperazine to obtain the title substance (a L-erythro isomer; 204.2 mg) as a white solid.

$^1$H-NMR (CDCl$_3$): coincident with the data of the DL-erythro isomer of Example 2.

Example 17

Synthesis of (1S, 2R)-2-decanoylamino-3-(4-hydroxypiperidino)-1-phenyl-1-propanol According to the method of Example 16, synthesis was carried out in the same manner by using (1S, 2R)-2-benzyloxycarbonylamino-1-phenyl-1,3-propanediol-3-methanesulfonyl ester in place of (1R, 2S)-2-benzyloxycarbonylamino-1-phenyl-1,3-propanediol-3-methanesulfonyl ester to obtain the title substance (a D-erythro isomer; 160.5 mg) as a colorless oily product.

$^1$H-NMR (CDCl$_3$): coincident with the data of the DL-erythro isomer of Example 2.

Example 18

Synthesis of (1R, 2R)-2-decanoylamino-3-(4-hydroxypiperidino)-1-phenyl-1-propanol According to the method of Example 16, synthesis was carried out in the same manner by using (1R, 2R)-2-benzyloxycarbonylamino-1-phenyl-1,3-propanediol-3-methanesulfonyl ester in place of (1R, 2S)-2-benzyloxycarbonylamino-1-phenyl-1,3-propanediol-3-methanesulfonyl ester to obtain the title substance (a D-threo isomer; 184.2 mg) as a colorless oily product.

$^1$H-NMR (CDCl$_3$): coincident with the data of the DL-threo isomer of Example 2.

Example 19

Synthesis of (1R, 2S)-2-decanoylamino-3-diethylamino-1-phenyl-1-propanol

According to the method of Example 8, synthesis was carried out in the same manner by using (1R, 2S)-2-benzyloxycarbonylamino-1-phenyl-1,3-propanediol-3-methanesulfonyl ester in place of (1S, 2S)-2-benzyloxycarbonylamino-1-phenyl-1,3-propanediol-3-methanesulfonyl ester and using diethylamine in place of N-methylpiperazine to obtain the title substance (an L-erythro isomer).

$^1$H-NMR (CDCl$_3$): coincident with the data of the DL-erythro isomer of Example 3.

Example 20

Synthesis of (1S, 2R)-2-decanoylamino-3-diethylamino-1-phenyl-1-propanol

According to the method of Example 8, synthesis was carried out in the same manner by using (1S, 2R)-2-benzyloxycarbonylamino-1-phenyl-1,3-propanediol-3-methanesulfonyl ester in place of (1S, 2S)-2-benzyloxycarbonylamino-1-phenyl-1,3-propanediol-3-methanesulfonyl ester and using diethylamine in place of N-methylpiperazine to obtain the title substance (a D-erythro isomer).

$^1$H-NMR (CDCl$_3$): coincident with the data of the DL-erythro isomer of Example 3.

Example 21

Synthesis of (1R, 2S)-2-hexanoylamino-3-(4-hydroxypiperidino)-1-phenyl-1-propanol According to the method of Example 16, synthesis was carried out in the same manner by using hexanoyl chloride in place of decanoyl chloride to obtain the title substance (250.5 mg) as a white solid.

$^1$H-NMR (CDCl$_3$): 7.36-7.26 (5H, m, aromatic), 5.95 (1H, d, J=4.3Hz, NH), 4.80 (1H, d, J=5.0 Hz, H-1), 4.22 (1H, m, H-2), 3.72 (1H, m, H-4'), 2.90-2.78 (2H, br, H-2'A), 2.70-2.56 (2H, m, H-3), 2.38-2.35 (2H, br, H-2'B), 2.01-1.91 (2H, br, H-3'A), 2.16-2.10 (2H, m, COCH$_2$), 1.67-1.57 (4H, m, H-3'B, COCH$_2$CH$_2$), 1.24 (4H, brs, (CH$_2$)$_2$CH$_3$), 0.88 (3H, t, CH$_3$)

Example 22

Synthesis of (1R, 2S)-2-octanoylamino-3-(4-hydroxypiperidino)-1-phenyl-1-propanol According to the method of Example 16, synthesis was carried out in the same manner by using octanoyl chloride in place of decanoyl chloride to obtain the title substance (230.2 mg) as a white solid.

$^1$H-NMR (CDCl$_3$): 7.36-7.26 (5H, m, aromatic), 6.09 (1H, d, J=4.3Hz, NH), 4.80 (1H, d, J=5.0Hz, H-1), 4.21 (1H, m, H-2), 3.70 (1H, m, H-4'), 2.90-2.78 (2H, br, H-2'A), 2.70-2.56 (2H, m, H-3), 2.38-2.35 (2H, br, H-2'B), 2.01-1.91 (2H, br, H-3'A), 2.16-2.10 (2H, m, COCH$_2$), 1.67-1.57 (4H, m, H-3'B, COCH$_2$CH$_2$), 1.24 (8H, brs, (CH$_2$)$_4$CH$_3$), 0.88 (3H, t, CH$_3$)

Example 23

Synthesis of (1R, 2S)-2-dodecanoylamino-3-(4-hydroxypiperidino)-1-phenyl-1-propanol According to the method of Example 16, synthesis was carried out in the same manner by using dodecanoyl chloride in place of decanoyl chloride to obtain the title substance (265.0 mg) as a white solid.

$^1$H-NMR (CDCl$_3$): 7.36-7.26 (5H, m, aromatic), 5.97 (1H, d, J=4.3Hz, NH), 4.80 (1H, d, J=5.0Hz, H-1), 4.22 (1H, m, H-2), 3.72 (1H, m, H-4'), 2.90-2.78 (2H, br, H-2'A), 2.70-2.56 (2H, m, H-3), 2.38-2.35 (2H, br, H-2'B), 2.01-1.91 (2H, br, H-3'A), 2.16-2.10 (2H, m, COCH$_2$), 1.67-1.57 (4H, m, H-3'B, COCH$_2$CH$_2$), 1.24 (16H, brs, (CH$_2$)$_8$CH$_3$), 0.88 (3H, t, CH$_3$)

Examples 24 to 26

By the same method as in Examples 21 to 23, the following stereoisomers were synthesized. The yields are as shown below.

Example 24

(1S, 2R)-2-hexanoylamino-3-(4-hydroxypiperidino)-1-phenyl-1-propanol; yield: 245.0 mg Example 25

(1S, 2R)-2-octanoylamino-3-(4-hydroxypiperidino)-1-phenyl-1-propanol; yield: 233.5 mg Example 26

(1S, 2R)-2-dodecanoylamino-3-(4-hydroxypiperidino)-1-phenyl-1-propanol; yield: 215.0 mg Example 27

MDCK cells which were cells derived from canine kidney were cultured in an Eagle's medium containing 10% bovine fetal serum for 4 days (7.5×10$^4$ cells/0.25 ml). The cells were infected with 0.002 PFU/0.5 ml of A/PR/8/34 strain influenza virus. After 30 minutes, the compounds (in the formula (I), R$^1$=phenyl, R$^{11}$=a hydrogen atom and n=7) of the present invention shown in Table 1 were added thereto at a concentration of 10 µM, and the mixtures were further cultured at 37° C. for 3 days. Then, the survival rate (%) of the cells was measured according to the MTT method (Pauwels et al, J. Virol. Methods, Vol. 20, pp. 309–321, (1988)) and shown as a cytopathic effect (CPE).

Further, a virus growth-inhibiting rate (%) (a reduction rate of a sialidase activity) was calculated by measuring the activities of sialidase derived from influenza virus in the supernatants of the MDCK cell culture broths treated with the compounds of the present invention at a concentration of 10 µM. These results are shown in Table 1. Further, the compounds of the present invention were used at a concentration range of 0.5 to 10 µM, and an antiviral action was measured in the same manner as described above to determine a concentration at which the cytopathic effect derived from virus was reduced by 50% as compared with a control (to which no medicine was added), which is shown in Table 1.

Further, in order to evaluate the cytotoxicities to the MDCK cells of the compounds of the present invention, these compounds at the same concentration were added to cells which were not infected with virus, and the survival rate after carrying out culture in the same manner was examined by the MTT method, which is also shown in Table 1.

TABLE 1

Antiviral action of 2-acylaminopropanol compounds

| Compound (R$^2$) (10 µM) | | Virus growth inhibition (%) | Cytopathic effect (%) | ED$_{50}$ (µM) | Cytotoxicity of compound (survival rate (%) of cells) |
|---|---|---|---|---|---|
| Example | | | | | |
| Control | | 0 | 80.0 | | 100 |
| —N(piperidino) | (DL-threo) (DL-erythro) | 93.9 99.6 | 40.0 7.8 | | 80 to 100 80 to 100 |
| —N(4-hydroxypiperidino)—OH | (DL-threo) (DL-erythro) | 87.3 100 | 14.2 0 | 5.4 5.0 | 100 100 |
| —N(pyrrolidino) | (DL-erythro) | 88.5 | 9.9 | 1.5 | 100 |
| —N(3-hydroxypiperidino)OH | (Mixture of isomers) | 99.7 | 3.1 | 1.5 | 80 to 100 |

TABLE 1-continued

Antiviral action of 2-acylaminopropanol compounds

| Compound (R²) (10 μM) | Virus growth inhibition (%) | Cytopathic effect (%) | $ED_{50}$ (μM) | Cytotoxicity of compound (survival rate (%) of cells) |
|---|---|---|---|---|
| Comparative example | | | | |
| —N(morpholine) (D-threo-PDMP) | 97.1 | 44.8 | | 60 to 80 |

As can be clearly seen from Table 1, it was confirmed that the compounds of the present invention exhibit clearly stronger antiviral activities than Comparative example (PDMP), and almost no cytotoxicity is observed so that they are useful as an antiviral agent.

Example 28

In the same manner as in Example 27, the D-erythro isomers and the L-erythro isomers of the compounds of the present invention synthesized in Examples 16, 17, 19 and 20 were used respectively, and the virus growth rates (%) and the cell survival rates (%) were measured in the same manner by using A/PR/8/34 strain influenza virus, A/Guizhou/54/89 strain influenza virus and B/Ibaraki/2/85 strain influenza virus.

Figure 1B:
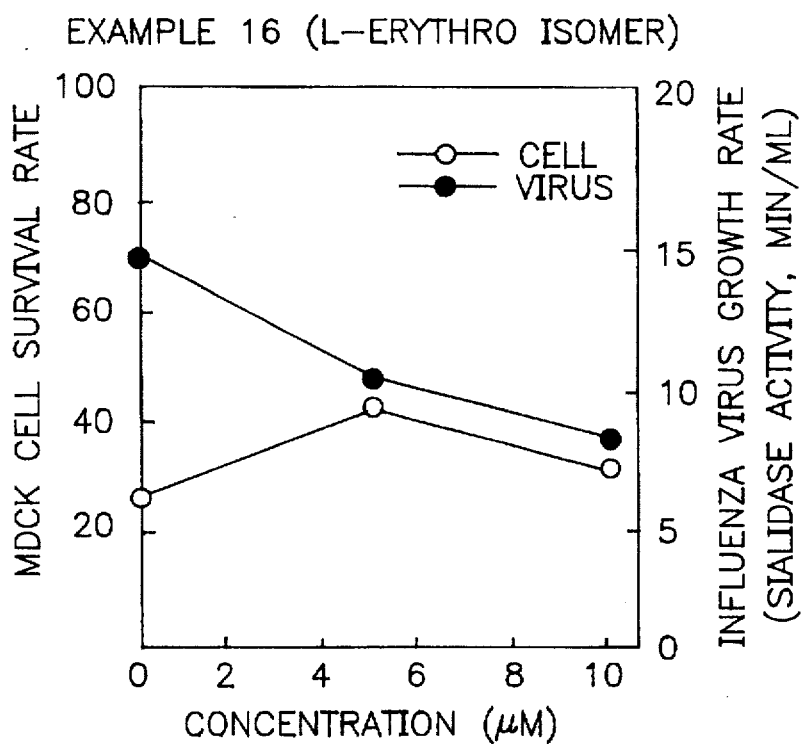
Figure 1C:
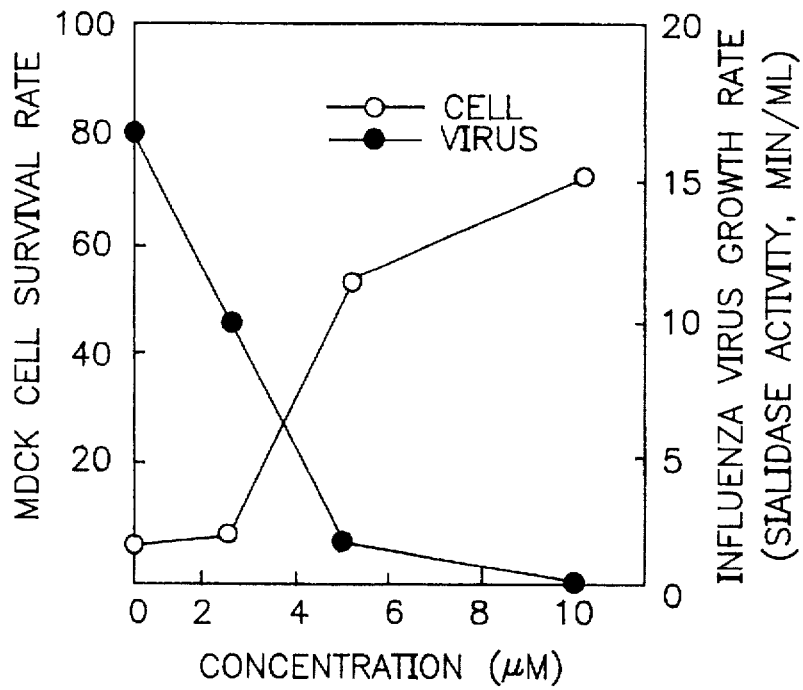
Figure 1D:
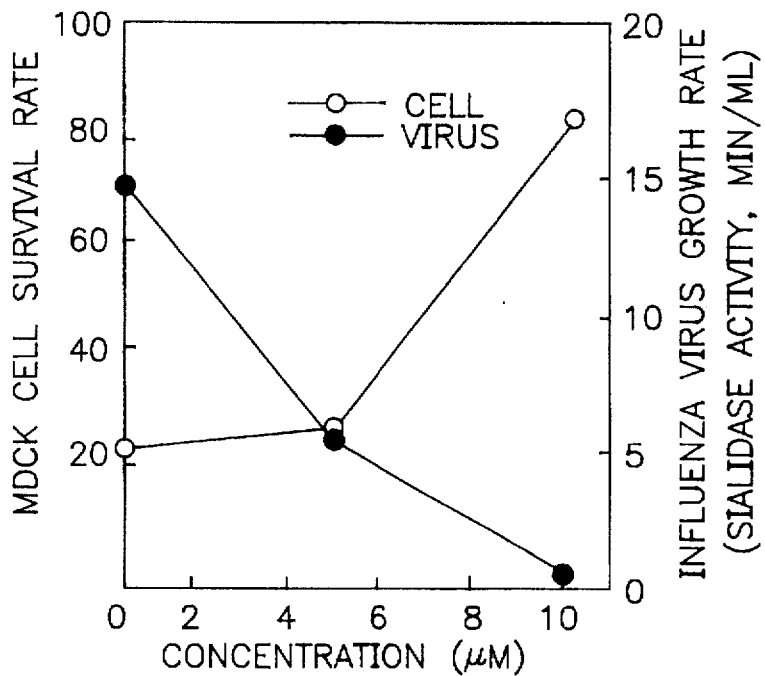
Figure 2A:
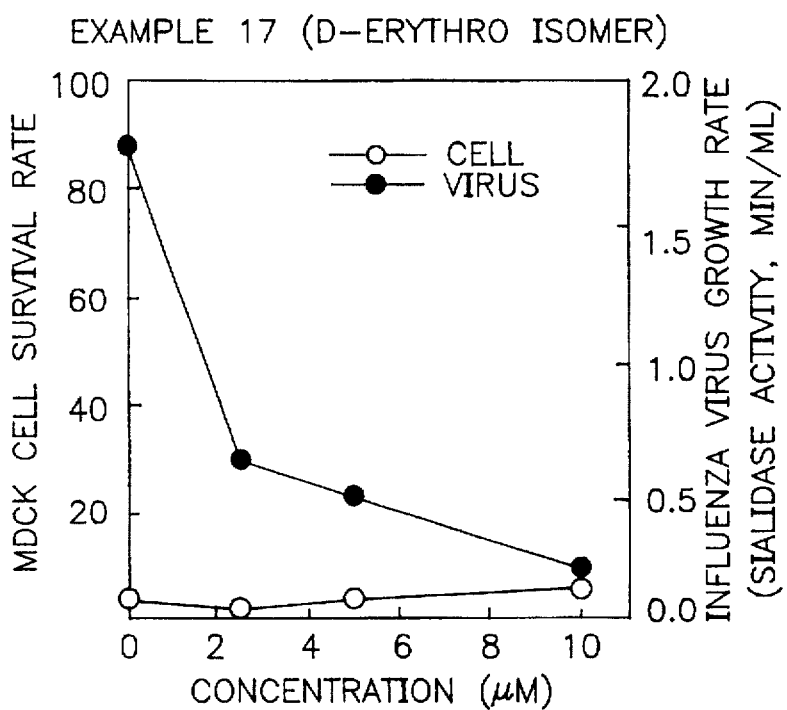
Figure 2B:
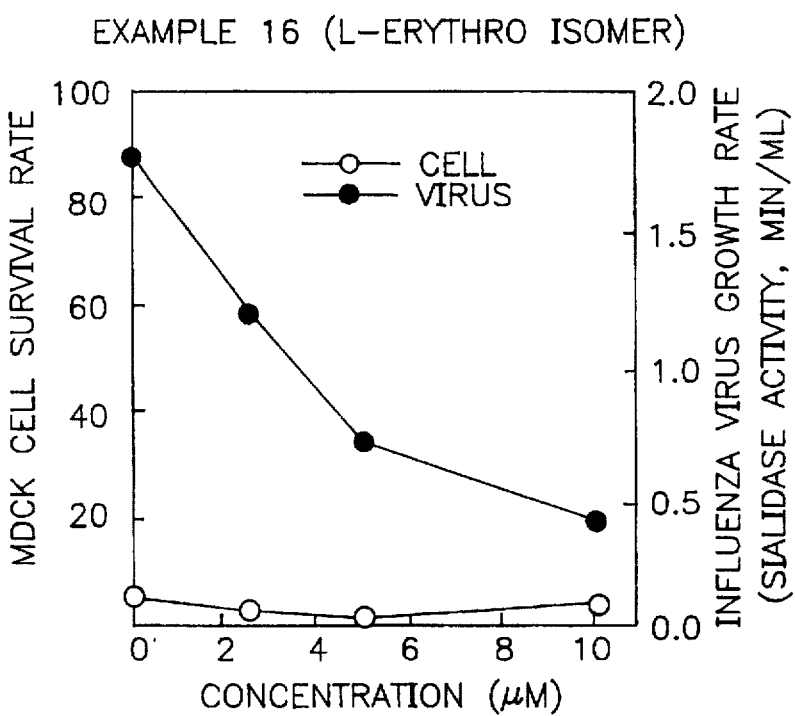
Figure 2C:
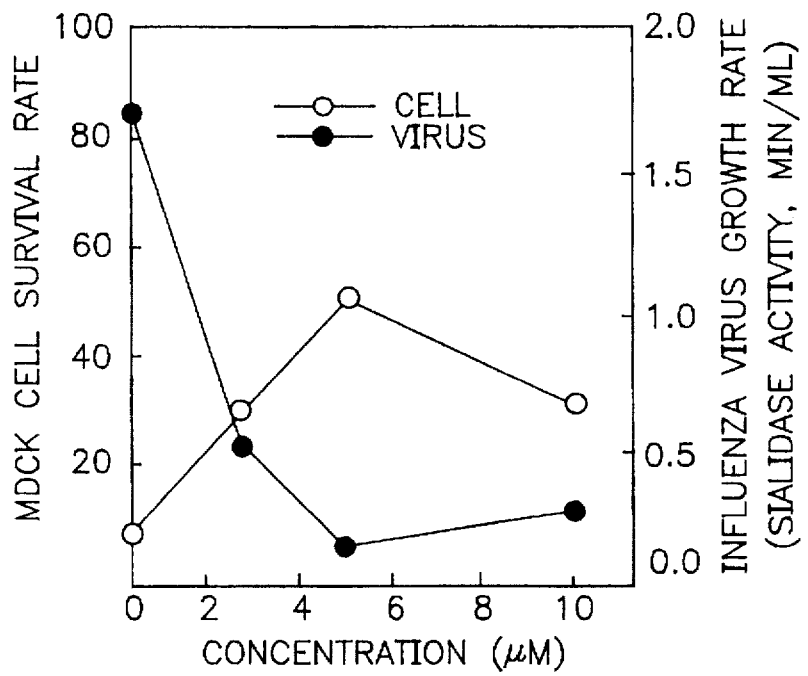
Figure 2D:
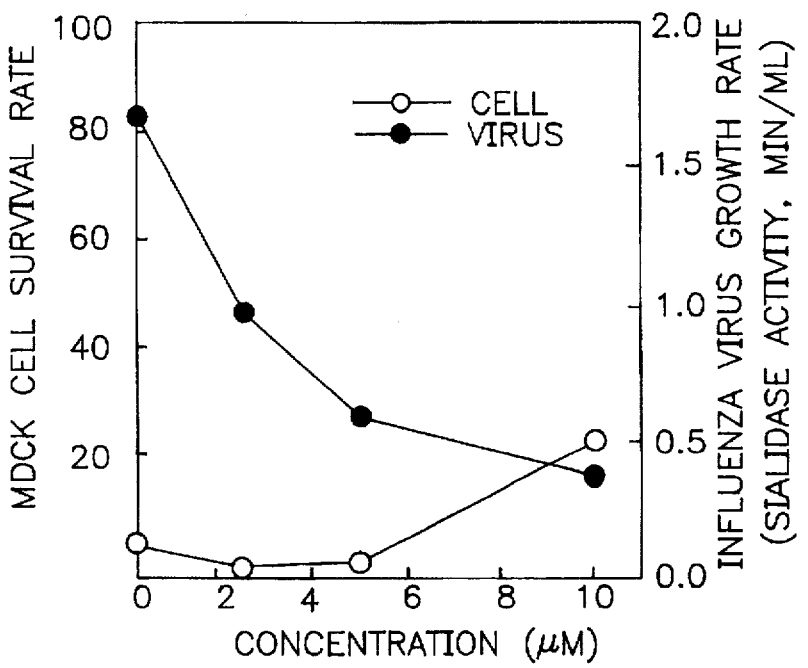
Figure 3A:
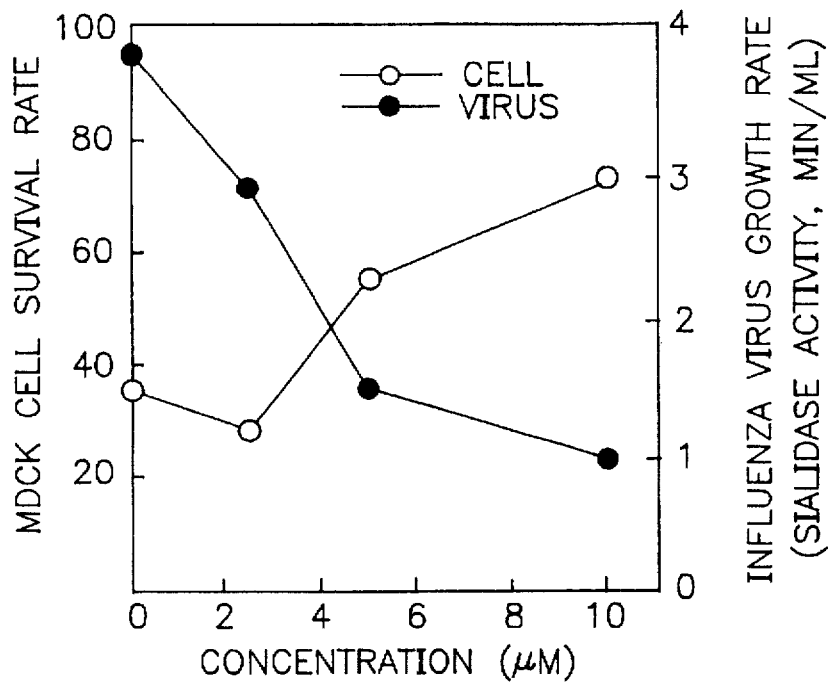
Figure 3B:
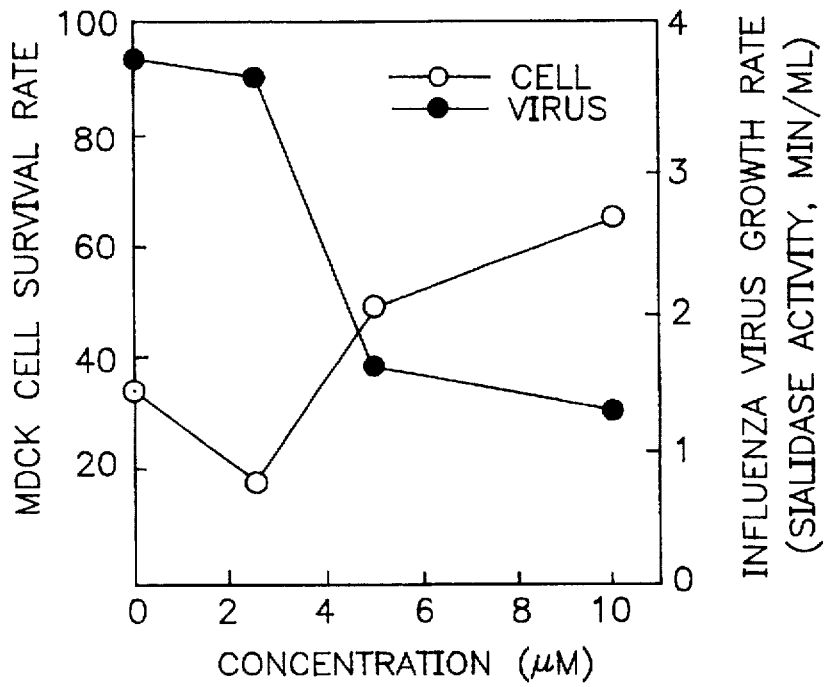
Figure 3C:
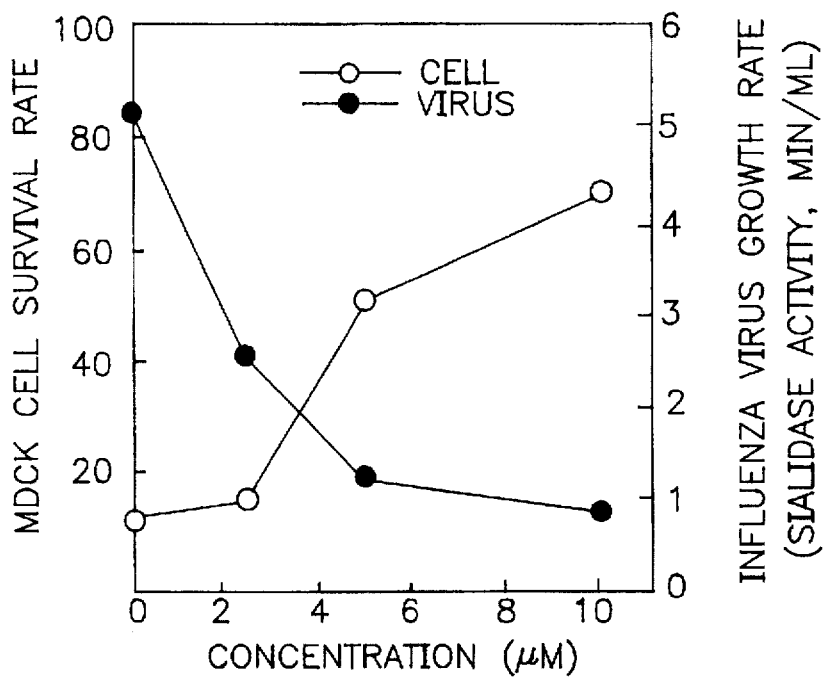
Figure 3D:
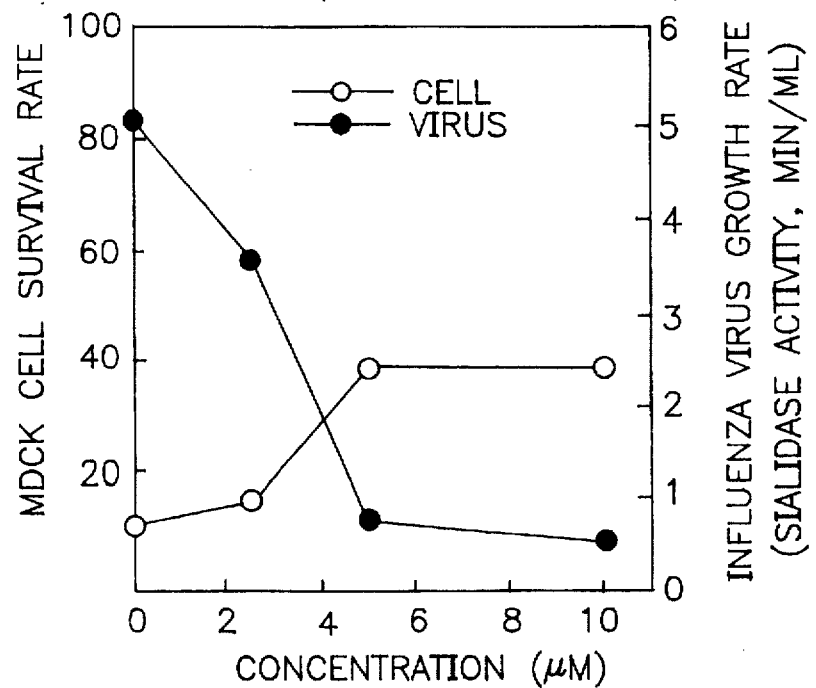

The results are shown in FIGS. 1 to 3.

BRIEF DESCRIPTION OF DRAWINGS

In the figures, ○ is a value obtained by estimating the effect of the medicine exerted on the virus-infected MDCK cells with the survival rate of the cells when no virus was added being a control (100%), and ● is a value obtained by estimating the effect of the medicine exerted on growth of influenza virus, by measuring the activity of sialidase derived from virus.

As can be clearly seen from FIGS. 1 to 3, it was confirmed that the compounds of the present invention inhibit growth of influenza virus and further increase the survival rate of the MDCK cells infected with virus.

Example 29

B16 melanoma cells derived from neuroectoderm were put into a culture plate with 12 wells in an amount of $2 \times 10^5$ cells/well and cultured for 24 hours in Dulbecco modified Eagle's media containing 10% bovine fetal serum. Thereafter, the media were exchanged with the same culture broths containing 2-acylaminopropanol compounds shown in Table 2, and $^{14}C$-galactose was added thereto. After 24 hours, the media were removed, the cells were washed with 1 ml of a phosphate buffer containing 0.02% EDTA, 1 ml of 0.25 % trypsin was added, and the mixtures were left to stand at 37° C. for 5 minutes. The cells were recovered by using the same culture broths and washed with a phosphate buffer, and then masses of the cells were obtained. 4 ml of methanol and chloroform were added successively to the masses of the cells to extract all GSL, followed by evaporation to dryness. Next, after this all GSL was suspended in 1 ml of water, the suspensions were dialyzed to water for 2 days to completely remove low molecules such as $^{14}C$-galactose, etc. The radioactivities of the GSL fractions thus obtained were measured by a liquid scintillation counter. The results are shown in Table 2. A control is a result of carrying out an experiment in the same manner by exchanging the medium with the same amount of a culture broth not containing the compound of the present invention.

TABLE 2

Glycolipid biosynthesis-accelerating action of 2-acylaminopropanol compounds

| | Compound | | Treatment concentration (μM) | Uptake of $^{14}C$-galactose into GSL fraction (cpm/mg protein) | Glycolipid biosynthesis acceleration (%) |
|---|---|---|---|---|---|
| | Control | | | 6,100 | 100 |
| 1 | 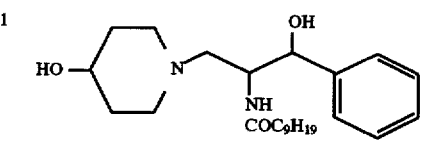 | D-erythro<br>L-threo | 10 μM<br>10 μM | 11,470<br>9,670 | 188<br>159 |
| 2 | 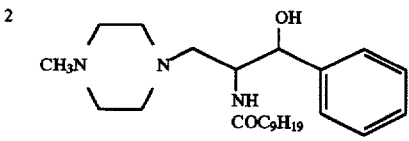 | L-threo | 10 μM | 10,300 | 169 |

TABLE 2-continued

Glycolipid biosynthesis-accelerating action of 2-acylaminopropanol compounds

| Compound | | Treatment concentration (μM) | Uptake of $^{14}$C-galactose into GSL fraction (cpm/mg protein) | Glycolipid biosynthesis acceleration (%) |
|---|---|---|---|---|
| 3 | 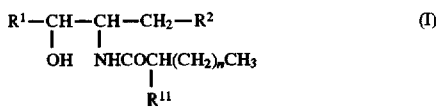 | L-threo 10 μM | 9,380 | 161 |
| 4 | 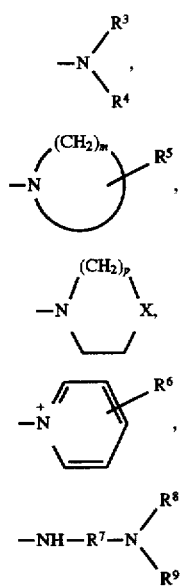 | L-threo 5 μM | 9,740 | 160 |

As can be clearly seen from Table 2, it was found that the D-erythro isomer of Compound 1 and the L-threo isomers of Compounds 1, 2, 3 and 4 significantly accelerate biosynthesis of glycolipids including ganglioside, and the possibility that they have an effect of improving the function of neurocytes was suggested. Therefore, it can be said that the compounds of the present invention are effective for treating and preventing neuronal diseases.

We claim:

1. A 2-acylaminopropanol compound of the formula $$R^1-CH-CH-CH_2-R^2 \quad (I)$$
$$\phantom{R^1-}|\phantom{CH-}|$$
$$\phantom{R^1-}OH\phantom{CH-}NHCOCH(CH_2)_nCH_3$$
$$\phantom{R^1-OH-NHCOCH(CH_2)_n}|$$
$$\phantom{R^1-OH-NHCOCH(CH_2)_n}R^{11}$$

wherein $R^1$ is phenyl optionally substituted by 1 to 3 members selected from the group consisting of alkyl, alkoxy, hydroxyl, hydroxyalkyl and nitro, $R^2$ is a formula selected from the group consisting of $$-N\begin{matrix}R^3\\R^4\end{matrix} \quad (II)$$

$$-N\begin{matrix}(CH_2)_m\\ \phantom{()}\end{matrix}R^5 \quad (III)$$

$$-N\begin{matrix}(CH_2)_p\\ \phantom{()}\end{matrix}X, \quad (IV)$$

$$-\overset{+}{N}\begin{matrix}\phantom{()}\\ \phantom{()}\end{matrix}R^6 \quad (V)$$

$$-NH-R^7-N\begin{matrix}R^8\\R^9\end{matrix} \quad (VI)$$

wherein $R^3$ and $R^4$ are individually selected from the group consisting of hydrogen, alkyl of 1 to 6 carbon atoms, alkenyl, hydroxyalkyl, alkoxyalkyl, aminoalkyl, cycloalkyl, hydroxycycloalkyl, aralkyl and piperazino optionally substituted by alkyl, $R^5$ is 1 or 2 substituents selected from the group consisting of hydrogen, hydroxyl, lower alkyl, alkoxy, hydroxyalkyl, carboxy, alkoxycarbonyl, aralkyl, piperidino, acyloxy, of an organic carboxylic acid amino and aminoalkyl, $R^6$ is hydrogen or 1 or 2 substituents of $R^5$, $R^7$ is alkylene optionally interrupted by oxygen, $R^8$ and $R^9$ are individually selected from the group consisting of hydrogen, lower alkyl and hydroxy-lower alkyl, or $R^8$ and $R^9$ together with the nitrogen atom to which they are bonded form a piperidino or morpholino optionally substituted by lower alkyl, m is an integer of 2 to 6, p is 2 or 3, X is $$\begin{matrix}\diagdown\\ \phantom{()}N-R^{10},\\ \diagup\end{matrix} \quad (VII)$$

or $$\begin{matrix}\diagdown\\ \phantom{()}S\\ \diagup\end{matrix} \quad (VIII)$$

wherein $R^{10}$ is selected from the group consisting of hydrogen, lower alkyl, acyl, lower alkoxycarbonyl and pyridyl, $R^{11}$ is hydrogen or hydroxyl and n is an integer of 3 to 15) or a non-toxic, pharmaceutically acceptable salt thereof.

2. The 2-acylaminopropanol compound according to claim 1 or a pharmaceutically acceptable salt thereof, wherein $R^1$ is phenyl optionally substituted by 1 or 2 hydroxyl or alkyl or alkoxy of 1 to 4 carbon atoms.

3. The 2-acylaminopropanol compound according to claim 1 or a pharmaceutically acceptable salt thereof, wherein $R^1$ is phenyl group optionally substituted by 1 or 2 hydroxyl groups or methoxy groups.

4. The 2-acylaminopropanol compound according to claim 1 or a pharmaceutically acceptable salt thereof, wherein $R^2$ is a substituent of formula (II), and $R^3$ and $R^4$ are selected from the group consisting of alkyl of 1 to 6 carbon atoms, alkenyl of 3 to 4 carbon atoms, alkoxyalkyl of 3 to 6 carbon atoms, cycloalkyl of 5 to 8 carbon atoms and phenylalkyl of 7 to 9 carbon atoms.

5. The 2-acylaminopropanol compound according to claim 1 or a pharmaceutically acceptable salt thereof, wherein $R^2$ is a substituent of formula (II), and $R^3$ and $R^4$ are individually selected from the group consisting of methyl, ethyl, propyl, isopropyl, butyl, isobutyl, heptyl, hexyl, allyl, 1-propenyl, 2-butenyl, hydroxyethyl, methoxyethyl, ethoxyethyl, aminoethyl, cyclopentyl, cyclohexyl, 4-hydroxycyclohexyl, benzyl, α-methylbenzyl piperazino and 4-methyl-piperazino.

6. The 2-acylaminopropanol compound according to claim 1 or a pharmaceutically acceptable salt thereof, wherein $R^2$ is amino; methylamino, ethylamino, isopropylamino, isobutylamino, dimethylamino, diethylamino-, dipropylamino, methyl(ethyl)amino; 2-hydroxyethylamino, bis(2-hydroxyethyl)amino; 2-aminoethylamino; cyclohexylamino, 4-hydroxycyclohexylamino; benzylamino or α-methylbenzylamino.

7. The 2-acylaminopropanol compound according to claim 1 or a pharmaceutically acceptable salt thereof, wherein $R^2$ is a substituent of formula, and $R^5$ is selected from the group consisting of alkyl of 1 to 4 carbon atoms, methoxy, ethoxy, hydroxymethyl, 2-hydroxyethyl, methoxycarbonyl, ethoxycarbonyl, benzyl acetoxy and aminomethyl.

8. The 2-acylaminopropanol compound according to claim 1 or a pharmaceutically acceptable salt thereof, wherein $R^2$ is selected from the group consisting of ethyleneimino, azetidino, pyrrolidino, piperidino, azepino, 2- or 3-hydroxypyrrolidino, 2-hydroxymethyl-pyrrolidino, 2-, 3- or 4-hydroxypiperidino, 3, 4-dihydroxy piperidino, 2-, 3- or 4-hydroxymethylpiperidino, 2-, 3- or 4-hydroxyethylpiperidino, 2-, 3- or 4-methylpiperidino, 3,5-dimethylpiperidino, 3-hydroxymethyl-4,5-dihydroxypiperidino, 2-hydroxymethyl-3,4,5-trihydroxypiperidino, 4-methoxypiperidino, 4-methoxycarbonylpiperidino, 4-carboxypiperidino, 4-ethyoxycarbonylpiperidino, 4-benzylpiperidino or 4-piperidinopiperidino.

9. The 2-acylaminopropanol compound according to claim 1 or a pharmaceutically acceptable salt thereof, wherein $R^2$ is a substituent of formula (IV) and is selected from the group consisting of 4-thiazinyl, thiomorpholino, piperazino, N-methylpiperazino, N-methoxycarbonylpiperazino, N-ethyoxycarbonylpiperazino, N-(2-pyridyl)piperazino, N-formylpiperazino, N-acetylpiperazino and N-methyl-1,4-diazacycloheptan-1-yl.

10. The 2-acylaminopropanol compound according to claim 1 or a pharmaceutically acceptable salt thereof, wherein $R^2$ is a substituent of formula (VI) and is selected from the group consisting of 2-(dimethylamino)ethylamino, 2-(methylamino)ethylamino, 2-(diethylamino)ethylamino, 2-(ethylamino)ethylamino, 3-(dimethylamino)propylamino, 3-(diethylamino)propylamino, 3-(dibutylamino)propylamino, 3-[[di]bis(2-hydroxyethyl)amino]-propylamino, 3-2-dimethylamino)ethoxy)propylamino, 2-piperidinoethylamino, 2-(4-methylpiperidino)ethylamino, 3-piperidinopropylamino, 3-(2-methylpiperidino)propylamino, 3-(4-methylpiperidino)propylamino, 2-morpholinoethylamino and 3- morpholinopropylamino.

11. The 2-acylaminopropanol compound according to claim 1 or a pharmaceutically acceptable salt thereof, wherein $R^1$ is phenyl optionally substituted by 1 to 2 substituents selected from the group consisting of hydroxyl and methoxy, $R^2$ is formula (II), (III), or (IV) wherein in the formula (II), $R^3$ and $R^4$ are the same alkyl of 1 to 3 carbon atoms or $R^3$ is hydrogen and $R^4$ is cycloalkyl or hydroxycycloalkyl of 5 to 6 carbon atoms;

in the formula (III), $R^1$ is hydrogen or hydroxyl and m is 4 or 5, in the formula (IV), p is 2, X is formula (VII) and $R^{10}$ is methyl, $R^{11}$ is hydrogen and n is an integer of 5 to 13.

12. The 2-acylaminopropanol compound according to claim 1 or a pharmaceutically acceptable salt thereof, wherein $R^1$ is phenyl optionally substituted by 1 to 2 substituents selected from the group consisting of hydroxyl and methoxy, $R^2$ is a dimethylamino group, a diethylamino group, a cyclohexylamino group, a 4-hydroxycyclohexylamino group, a pyrrolidino group, a 3-hydroxypyrrolidino group, a piperidino group, a 4-hydroxypiperidino group or a N-methylpiperazino group; $R^{11}$ is a hydrogen atom; and n is an integer of 5 to 13.

13. The 2-acylaminopropanol compound according to claim 1 or a pharmaceutically acceptable salt thereof, wherein $R^1$ is phenyl, $R^2$ is selected from the group consisting of diethylamino, 4-hydroxypiperidino, N-methylpiperazino and 3-hydroxypyrrolidino, $R^{11}$ is hydrogen, and n is 5 to 13.

14. A medical composition which comprises the 2-acylaminopropanol compound according to claim 1 or a pharmaceutically acceptable salt thereof as an active ingredient.

15. The medical composition according to claim 14, wherein the 2-acylaminopropanol compound according to claim 1 or a pharmaceutically acceptable salt thereof is administered in an amount of 0.25 to 200 mg/kg per day.

16. The medical composition according to claim 15, wherein the 2-acylaminopropanol compound according to claim 1 or a pharmaceutically acceptable salt thereof is administered in an amount of 0.5 to 100 mg/kg per day.

17. An antiviral agent which comprises the 2-acylaminopropanol compound according to claim 1 or a pharmaceutically acceptable salt thereof as an active ingredient.

18. The antiviral agent according to claim 17, wherein in the formula (I), $R^1$ is phenyl optionally substituted by 1 to 2 hydroxyl or methoxy, $R^2$ is selected from the group consisting of dimethylamino, diethylamino, dipropylamino, piperidino, 4-hydroxypiperidino and 2-hydroxymethylpiperidino, $R^{11}$ is hydrogen or hydroxyl and n is an integer of 5 to 13, and the compound is a D-erythro isomer (1S, 2R) or a L-erythro isomer (1R, 2S).

19. The antiviral agent according to claim 17, wherein in the formula (I), $R^1$ is a phenyl group; $R^2$ is a diethylamino group or a 4-hydroxypiperidino group; $R^{11}$ is a hydrogen atom; and n is an integer of 7 to 13, and the compound is a D-erythro isomer (1S, 2R).

20. An agent for treating neuronal diseases, which comprises the 2-acylaminopropanol compound according to claim 1 or a pharmaceutically acceptable salt thereof as an active ingredient.

21. The agent for treating neuronal diseases according to claim 20, wherein in the formula (I), $R^1$ is phenyl optionally substituted by 1 to 2 hydroxyl or methoxy, $R^2$ is selected from the croup consisting of 4-hydroxycyclohexylamino, 3-hydroxypyrrolidino, 4-hydroxypiperidino, 3,4-dihydroxypiperidino, 3,4,5-trihydroxypiperidino, 3-hydroxymethyl-4,5-dihydroxypiperidino and N-methylpiperazino, $R^{11}$ is hydrogen or hydroxyl and n is an integer of 5 to 13, and the compound is L-threo isomer (1S, 2S), a D-erythro isomer (1S, 2R) or a L-erythro isomer (1R, 2S).

22. The agent for treating neuronal diseases according to claim 20, wherein in the formula (I), $R^1$ is phenyl, $R^2$ is selected from the group consisting of 4-hydroxycyclohexylamino, 3-hydroxypyrrolidino, 4-hydroxypiperidino and N-methylpiperazino $R^{11}$ is hydrogen and n is an integer of 5 to 13, and the compound is the L-threo isomer (1S, 2S).

23. The agent for treating neuronal diseases according to claim 20, wherein in the formula (I), $R^1$ is phenyl optionally substituted by 1 to 2 hydroxyl or methoxy, $R^2$ is selected from the group consisting of cyclohexylamino, pyrrolidino and piperidino, $R^{11}$ is hydrogen or hydroxyl and n is an integer of 5 to 13, and the compound is the D-threo isomer (1R, 2R).

24. The agent for treating neuronal diseases according to claim 20, wherein in the formula (I), $R^1$ is phenyl, $R^2$ is selected from the group consisting of cyclohexylamino, pyrrolidino and piperidino group; $R^{11}$ is hydrogen and n is an integer of 7 to 13, and the compound is a D-threo isomer (1R, 2R).

25. A method of treating viral infectious diseases in warm-blooded animals which comprises administering to warm-blooded animals an antivirally effective amount of a 2-acylaminopropanol compound according to claim 1 or a pharmaceutically acceptable salt thereof which are infected with viruses.

26. A method of treating neuronal diseases in mammals which comprises administering to mammals an amount of a 2-acylaminopropanol compound of formula (I) according to claim 1 or a pharmaceutically acceptable salt thereof effective for accelerating biosynthesis of glycosphingolipids, accelerating neurite extension and/or accelerating synapse formation which suffer form neuronal diseases caused by disorders of peripheral nervous system or central nervous system.

27. The 2-acylaminopropanol compound according to claim 1 or a pharmaceutically acceptable salt thereof, wherein $R^2$ is a substituent of formula (VI), the alkylene optionally interrupted by oxygen, of $R^7$ is selected from the group consisting of ethylene, trimethylene and —$(CH_2)_q$—O—$(CH_2)_r$—, q and r individually are 2 or 3, $R^8$ and $R^9$ are individually selected from the group consisting of methyl, ethyl, propyl, butyl and 2-hydroxyethyl, and $R^8$ and $R^9$ are together with the nitrogen atom to which they are bonded selected from the group consisting of piperidino, 2-, 3- or 4-methylpiperidino and morpholino.

\* \* \* \* \*